US006699678B1

(12) United States Patent
Ohana

(10) Patent No.: US 6,699,678 B1
(45) Date of Patent: Mar. 2, 2004

(54) *CHLAMYDIA TRACHOMATIS* SPECIFIC PEPTIDES AND THEIR USE IN DIAGNOSTIC ASSAYS

(75) Inventor: Bella Ohana, Rehovot (IL)

(73) Assignee: Savyon Diagnostics Ltd. (IL)

( * ) Notice: Subject to any disclaimer, the term of this patent is extended or adjusted under 35 U.S.C. 154(b) by 0 days.

(21) Appl. No.: 09/466,384

(22) Filed: Dec. 17, 1999

Related U.S. Application Data

(63) Continuation of application No. PCT/IL98/00276, filed on Jun. 15, 1998.

(30) Foreign Application Priority Data

Jun. 19, 1997 (IL) ............................................... 121115

(51) Int. Cl.[7] ........................ G01N 33/569; C12N 1/00; A61K 39/118; A61K 39/02

(52) U.S. Cl. ........................ 435/7.32; 435/7.1; 435/7.2; 435/7.36; 435/7.9; 435/7.92; 435/7.93; 435/7.94; 435/7.95; 435/71.1; 424/263.1; 424/185.1; 424/184.1; 424/139.1; 424/130.1; 530/300; 530/350

(58) Field of Search ......................... 435/7.1, 7.2, 7.32, 435/7.36, 7.9, 7.92, 7.93, 7.94, 7.95, 71.1; 530/300, 350; 424/130.1, 139.1, 263.1, 184.1, 185.1

(56) References Cited

U.S. PATENT DOCUMENTS

| | | | | |
|---|---|---|---|---|
| 4,427,782 A | | 1/1984 | Caldwell et al. | 436/542 |
| 5,318,892 A | | 6/1994 | Watanabe et al. | 435/7.36 |
| 5,770,714 A | * | 6/1998 | Agabian et al. | 536/23.1 |
| 5,869,608 A | * | 2/1999 | Caldwell et al. | 530/350 |
| 6,384,206 B1 | * | 5/2002 | Caldwell et al. | |

FOREIGN PATENT DOCUMENTS

| | | |
|---|---|---|
| EP | 0 192 033 B1 | 8/1986 |
| EP | 0 348 725 | 1/1990 |
| EP | 0 456 524 | 11/1991 |
| WO | WO 94/06827 | 3/1994 |
| WO | WO 95/11998 | 5/1995 |
| WO | WO 96/07910 | 3/1996 |

OTHER PUBLICATIONS

Bowie et al. Science, vol. 247: 1990; p. 1306; p. 1308.*
Houghten et al. Vaccines, 1986, Edited by Fred Brown: Cold Spring Harbor Laboratory.*
Collier 1961, The Lancet; 1: 795–800.*
Yuan, et al., Infect. Immun.57:1040–1049 (1989).
Melgosa, et al., Infect. Immun. 59:2195–2199 (1991).
Qu, Zhenai, et al., Vaccine 12(6):557–564 (1994).
U.S. Dep. Health & Human Service NTIS application No. U.S. 7,324,664 XP002085083 Aug. 29, 1989.

* cited by examiner

*Primary Examiner*—Lynette R. F. Smith
*Assistant Examiner*—Padma Basker
(74) *Attorney, Agent, or Firm*—Lerner, David, Littenberg, Krumholz & Mentlik, LLP

(57) ABSTRACT

Disclosed are peptides or a mixture of peptides, or analogs thereof, derived from the variable domains of the *Chlamydia trachomatis* (*C. trachomatis*) immunodominant major outer membrane protein (MOMP). The peptides or mixtures of peptides are characterized by having specificity only to *C. trachomatis* anti-MOMP antibodies and being non-cross reactive with anti-MOMP antibodies of other Chlamydia species Specific peptides are described (SEQ ID Nos. 1 to 8) as well as their analogs, which have essentially the same biological activity.

8 Claims, 12 Drawing Sheets

SEQUENCE LISTING

<160> NUMBER OF SEQ ID NOS: 14

<210> SEQ ID NO 1
<211> LENGTH: 17
<212> TYPE: PRT
<213> ORGANISM: Chlamydia trachomatis

<400> SEQUENCE: 1

Ile Phe Asp Thr Thr Leu Asn Pro Thr Ile Ala Gly Ala Gly Asp Val
1 5 10 15

Lys

<210> SEQ ID NO 2
<211> LENGTH: 18
<212> TYPE: PRT
<213> ORGANISM: Chlamydia trachomatis

<400> SEQUENCE: 2

Val Asp Ile Thr Thr Leu Asn Pro Thr Ile Ala Gly Cys Gly Ser Val
1 5 10 15

Ala Lys

<210> SEQ ID NO 3
<211> LENGTH: 19
<212> TYPE: PRT
<213> ORGANISM: Chlamydia trachomatis

<400> SEQUENCE: 3

Cys Val Phe Asp Val Thr Thr Leu Asn Pro Thr Ile Ala Gly Ala Gly
1 5 10 15

Asp Val Lys

<210> SEQ ID NO 4

-continued

<211> LENGTH: 23
<212> TYPE: PRT
<213> ORGANISM: Chlamydia trachomatis

<400> SEQUENCE: 4

Leu Ala Glu Ala Ile Leu Asp Val Thr Thr Leu Asn Pro Thr Ile Thr
1 5 10 15

Gly Lys Ala Val Val Ser Lys
20

<210> SEQ ID NO 5
<211> LENGTH: 23
<212> TYPE: PRT
<213> ORGANISM: Chlamydia trachomatis

<400> SEQUENCE: 5

Cys Asp Asn Glu Asn Gln Ser Thr Val Lys Thr Asn Ser Val Pro Asn
1 5 10 15

Met Ser Leu Asp Gln Ser Lys
20

<210> SEQ ID NO 6
<211> LENGTH: 15
<212> TYPE: PRT
<213> ORGANISM: Chlamydia trachomatis

<400> SEQUENCE: 6

Val Ala Gly Leu Glu Asn Asp Pro Thr Thr Asn Val Ala Arg Ala
1 5 10 15

<210> SEQ ID NO 7
<211> LENGTH: 22
<212> TYPE: PRT
<213> ORGANISM: Chlamydia trachomatis

<400> SEQUENCE: 7

Asp Asn Glu Asn Asn Ala Thr Val Ser Asp Ser Lys Leu Val Pro Asn
1 5 10 15

His Met Ser Asp Gln Ser
20

<210> SEQ ID NO 8
<211> LENGTH: 16
<212> TYPE: PRT
<213> ORGANISM: Chlamydia trachomatis

<400> SEQUENCE: 8

Leu Asp Val Thr Thr Asn Ala Thr Ile Ala Gly Lys Gly Thr Val Val
1 5 10 15

<210> SEQ ID NO 9
<211> LENGTH: 10
<212> TYPE: PRT
<213> ORGANISM: Chlamydia pneumoniae

<400> SEQUENCE: 9

Asn Tyr Thr Thr Ala Val Asp Arg Pro Asn
1 5 10

<210> SEQ ID NO 10
<211> LENGTH: 18
<212> TYPE: PRT
<213> ORGANISM: Chlamydia pneumoniae -continued

```
<400> SEQUENCE: 10

Ala Phe Pro Leu Pro Thr Asp Ala Gly Val Ala Thr Ala Thr Gly Thr
  1               5                  10                  15

Lys Ser


<210> SEQ ID NO 11
<211> LENGTH: 20
<212> TYPE: PRT
<213> ORGANISM: Chlamydia pneumoniae

<400> SEQUENCE: 11

Ser Leu Leu Gly Asn Ala Leu Ser Thr Thr Asp Ser Phe Ser Asp Phe
  1               5                  10                  15

Met Gln Ile Val
             20


<210> SEQ ID NO 12
<211> LENGTH: 29
<212> TYPE: PRT
<213> ORGANISM: Chlamydia pneumoniae

<400> SEQUENCE: 12

Cys Phe Ser Met Gly Ala Lys Pro Thr Gly Ser Ala Ala Ala Asn Tyr
  1               5                  10                  15

Thr Thr Ala Val Asp Arg Pro Asn Pro Ala Tyr Asn Lys
             20                  25


<210> SEQ ID NO 13
<211> LENGTH: 20
<212> TYPE: PRT
<213> ORGANISM: Chlamydia pneumoniae

<400> SEQUENCE: 13

Val Lys Gly Thr Thr Val Asn Ala Asn Glu Leu Pro Asn Val Ser Leu
  1               5                  10                  15

Ser Asn Gly Lys
             20


<210> SEQ ID NO 14
<211> LENGTH: 24
<212> TYPE: PRT
<213> ORGANISM: Chlamydia pneumoniae

<400> SEQUENCE: 14

Leu Asn Leu Thr Ala Trp Asn Pro Ser Leu Leu Gly Asn Ala Thr Ala
  1               5                  10                  15

Leu Ser Thr Thr Asp Ser Phe Lys
             20
```

*CHLAMYDIA TRACHOMATIS* SPECIFIC PEPTIDES AND THEIR USE IN DIAGNOSTIC ASSAYS

CROSS REFERENCE TO RELATED APPLICATIONS

This is a continuation of International Application No. PCT/IL98/00276 filed on Jun. 15, 1998, which claims priority on the basis of Israeli Patent Application 121115 filed Jun. 16, 1997, the content of which is hereby incorporated reference in its entirety.

FIELD OF THE INVENTION

The present invention concerns an improved method and kit for the diagnosis of *Chlamydia trachomatis* (*C. trachomatis*) in humans. More specifically, the present invention concerns a new mixture of peptides derived from the major outer membrane protein (MOMP), which together are capable of specifically reacting only with antibodies specific to any one of the serovars of *C. trachomatis*, and hence said mixture of peptides is particularly useful for identifying *C. trachomatis* infections in humans by binding specifically to antibodies, if present, in a body fluid sample obtained from an individual being tested.

BACKGROUND OF THE INVENTION

Chlamydia is a gram negative obligate intracellular bacteria that causes acute and chronic disease in mammalian and avian species. The genus Chlamydia is comprised of four species: *C. trachomatis, C. pneumonziae, C. precorum* and *C. psittaci.*

The *C. trachornatis* species is divided into 15 serovars. Serovars A, B, Ba and C are agents of trachoma, a leading cause of preventable blindness, endemic in the Third World. Serovars L1–L3 are the agents of lymphogranuloma venereum. Serovars D–K are a common cause of sexually transmitted genital infection worldwide: cervitis, endometritis/salpingitis in females and uretritis in both males and females. Endometritis/salpingitis can lead to agglutination of salpinx, with a higher risk of extra-uterine pregnancy and infertility. The genital infection can cause acute infection and persistent infection occasionally without any clinical sign. Generally, these infections are treatable, once they are diagnosed; however, without any treatment, the infections can progress to severe chronic inflammation leading to infertility, ectopic pregnancy, induced abortion or pre-term child delivery. Moreover, the infants of infected mothers can themselves be infected during birth, leading to conjunctivitis or pneumonia.

Serological testing, i.e., the testing for the presence (or not) of anti-*C. trachomatis* antibodies in an individual, is now an established approach in many countries, and has been shown to provide a comprehensive answer for the detection of *C. trachomatis* infection. In suspected deep-seated infections, body fluid sampling reduces the necessity for invasive procedures which are required for direct antigen detection. In cases of lower urogenital infections, collection limitations such as effectiveness of scrape sampling procedure, specimen handling and transportation difficulties have to be weighed. Above all, there however still remains the problematic issue that most Chlamydial infections are asymptomatic. Therefore, an infection may persist for a long time, ascend the upper genital tract, causing deep and chronic infections, and increase the probability of false negative results in procedures designed for direct antigen detection, i.e., sampling of lower genital tract tissue with anti-*C. trachomatis* antibodies, or other suitable procedures, to directly detect the presence of the major *C. trachomatis* antigens such as the major outer membrane protein (MOMP) indicative of Chlamydial infection.

Serological testing for *Chlamydia trachomatis*, through the detection of various specific antibodies, is today an effective and highly accepted optional detection procedure. New and refined technologies apply the immuno markers IgM, IgA and IgG to characterize the presence and stage of infection.

The detection of specific IgM antibodies is indicative of acute Chlamydial infections. The absence does not, however, preclude the presence of on-going infection, however, especially in recurrent and chronic cases. The detection of specific IgA antibodies is now accepted as indicative of active Chlamydial infection and has been shown to be an important marker because of the shorter lifetime of IgA antibodies which persist only as long as antigenic stimulation exists. IgA antibody detection is, moreover, suitable for post-therapy follow-up. IgG antibody detection is a marker for Chlamydial-positive immune-response, either for current, chronic or past infections.

There exists a high level of serological cross-reactions between the three different species of Chlamydia. Most of the serological diagnostic assays for Chlamydia use either purified elementary bodies (microimmunofluorescence, MIF and ELISA tests), lipopolysaccharide, LPS or purified major outer membrane protein, MOMP (ELISA tests) as antigens. Genus specific epitopes are present in all the above antigens, therefore, low species specificity is observed. Moreover, a large proportion of the worldwide human population has been exposed to *C. pneumoniae* (with no clinical signs) and the prevalence of anti-Chlamydia antibodies is very high. Therefore, the differentiation between *C. pneumoniae* and *C. trachomatis* specific antibodies using conventional serological screening tests (MIF, ELISA, EIA, etc.) is not very effective.

THE PRIOR ART

A number of publications have been made in which there have been disclosed the isolation, purification and characterization of the major *C. trachomatis* outer membrane complex proteins, including the above-noted MOMP, and the use thereof for the purposes of generating anti-*C. trachomatis* antibodies and in immunoassays to detect the presence of anti-*C. trachomatis* antibodies in samples obtained from individuals suspected of being infected by *C. trachomatis*. For example, in U.S. Pat. No. 5,318,892 and its corresponding EP 0 456 524, there is disclosed the use of *C. trachomatis* outer membrane complex consisting of at least three polypeptides, including MOMP, for assaying anti-*C. trachomatis* antibodies. In U.S. Pat. No. 4,427,782, there is described the isolation and characterization of the *C. trachomatis* MOMP and its use in immunoassays. However, in the aforesaid published patents, there is not provided any nucleotide or amino acid sequences of the MOMP polypeptide, nor is there disclosed the possibility of using peptides derived from MOMP for the purposes of immunization against *C. trachomatis* disease or for use in immunoassays to detect anti-*C. trachonzatis* antibodies, indicative of infection by *C. trachoniatis*. It is well known in the art that large proteins such as MOMP are less effective than smaller antigenic peptides derived therefrom, both for the purposes of immunization against *C. trachomatis* infection and for use in immunoassays to detect anti-*C. trachomatis* antibodies. Further, the complete MOMP protein obtained from *C. trachomatis* also has a number of epitopes which are common to the MOMP protein obtained from the other above-noted species of Chlamydia, with the result that using the complete protein in immunoassays to specifically detect anti-*C. trachomatis* antibodies is not reliable because of the possibility of cross-reactivity between the various Chlamydia species, with the result that when positive results are obtained, it is not readily possible to determine whether the antibodies are specific to *C. trachomatis* or to the other Chlamydia species. Hence, in respect of *C. trachomatis*, false-positive results may be obtained and may even lead to an incorrect diagnosis of the agent causing the infection and subsequently to an incorrect mode of treatment of the infection. Moreover, large proteins like MOMP are often also difficult to produce and purify, especially when high levels of purity are imperative when such proteins are to be used in diagnostic kits, and such large proteins are often difficult to incorporate into a kit, for example, a kit based on ELISA in which the antigen is usually immobilized on a solid support.

In other publications, there has been described the cloning and sequencing of MOMP derived from *C. trachomatis*, the production of recombinant *C. trachomatis* MOMP polypeptide and its use for raising anti-MOMP antibodies and its use in immunoassays to detect anti-MOMP antibodies specific to *C. trachomatis*. The aforesaid cloning and sequencing of MOMP has been described, for example, in EP 0 192 033, in which publication there is also described the production of various monoclonal antibodies, each recognizing a different specific epitope in MOMP. However, for the reasons noted above, even such a recombinant MOMP polypeptide still suffers from the drawbacks of having possible cross-reactivity with the MOMP proteins from the other Chlamydia species as regards recognition of anti-MOMP antibodies. Further, even recombinantly produced MOMP requires a significant input of resources and time, both for the production thereof and for the purification thereof, before it is suitable for use in diagnostic assays or as a vaccine.

A number of publications have described various peptides derived from MOMP which are useful as vaccines and also in immunoassays to detect anti-MOMP antibodies. To obtain such peptides has been possible following the elucidation of the full sequence of MOMP and its analysis with respect to variation of the sequence within the different serovars. For example, there has been described an analysis of the various domains of the *C. trachomatis* MOMP protein, namely, the fact that it is divided into four constant (CDI–IV) and four variable (VDI–IV) domains (Yuan et al. Infect. Immun. 57, p. 1040–1049, 1989). Based on such and similar data, peptides were designed that generally have sequences corresponding to those parts or regions of MOMP which were most variable, and therefore expected to also be most antigenic. This means that such peptides essentially represent epitopes of MOMP to which it is readily possible to raise antibodies and hence such peptides may be used as vaccines, or may be readily used in diagnostic assays to detect the presence of anti-MOMP antibodies. For example, in EP 0 348 725, there is described an epitope-specific peptide which is a common epitope of *C. trachomatis* that is useful for the production of specific antibodies to *C. trachomatis* MOMP and which peptide has a sequence derived from the MOMP sequence between amino acid residues 262 and 320. Further, in WO 94/06827, there is disclosed a synthetic peptide comprising a T-cell helper cell stimulating epitope and a B-cell neutralizing antibody stimulating epitope derived from the *C. trachomatis* MOMP. This synthetic peptide is useful in immunoassays to detect anti-*C. trachomatis* MOMP antibodies or as a vaccine. However, while the aforesaid peptides represent an important improvement over use of the complete MOMP polypeptide as regards their usefulness in diagnostic assays to detect *C. trachomatis* antibodies or their usefulness as vaccines, such peptides still suffer from one major drawback, namely, these peptides do not always define an epitope that is common to all of the above-noted serovars of *C. trachomatis*. As a result, when such peptides are used to detect *C. trachomatis* antibodies, they are not capable in all instances of detecting antibodies against all of the various serovars of *C. trachomatis* and subsequently false-negative results may be obtained in such diagnostic assays using such peptides, namely, an individual may have been infected with a certain serovar of *C. trachomatis* common to the area where such individual lives, but the peptide used in the assay may be one which does not fully correspond to the specific epitope of the specific serovar with which the individual has been infected with the result that antibodies raised in this individual will not react fully or will not react at all with the peptides in the diagnostic kit, resulting in the obtention of a false-negative result.

Hence, heretofore there has not been disclosed a *C. trachomatis* MOMP-specific peptide or mixture of peptides which are specific for all the different serovars of *C. trachomatis* and which may be used in diagnostic assays to detect anti-MOMP antibodies raised against any of the *C. trachomatis* serovars, or which may be used as vaccines to immunize people effectively against all of the various serovars of *C. trachomatis*. As mentioned above, *C. trachomatis* infections occur in a very large number of people worldwide and hence there has been a long-felt need to overcome the above-mentioned drawbacks of the prior art and to provide a peptide or mixture of peptides which may be used in diagnostic assays to detect anti-*C. trachomatis* MOMP antibodies raised in individuals following infection by any of the serovars of *C. trachomatis*. Likewise, it has been a long-felt need to provide a peptide or mixture of peptides, which when administered to an individual will be capable of eliciting anti-MOMP antibodies specific to any of the serovars of *C. trachomatis* and in this way provide for an effective vaccine against *C. trachomatis* infection.

SUMMARY OF THE INVENTION

Accordingly, it is an aim of the present invention to provide a mixture of peptides derived from specific regions within the MOMP protein, which together are capable of interacting with antibodies against MOMP from any of the serovars of *C. trachomatis*. Such a mixture of peptides is particularly useful for diagnostic assays to diagnose the presence of anti-MOMP antibodies specific to *C. trachomatis* obtained from the body fluids of an individual and being specific for all of the serovars of *C. trachomatis*, such diagnostic assays should essentially provide no false-negative results. Likewise, as the mixture of peptides is chosen, in accordance with the present invention, to be specific only to the MOMP of *C. trachomatis* serovars and not to MOMP from any other Chlamydia species, use of the peptides in such diagnostic assays should also provide these diagnostic assays as having essentially no false-positive results.

Another aim of the present invention is to provide for a diagnostic kit for diagnosing the presence in a body fluid of anti-*C. trachomatis* MOMP antibodies of any of the *C. trachomatis* serovars, this diagnostic kit, using such a mixture of peptides as noted above, providing for a highly reliable diagnostic test of test samples being inherently essentially incapable of yielding false-positive or false-negative results. This diagnostic kit is also highly specific only to anti-*C. trachomatis* MOMP antibodies and does not cross-react with anti-MOMP antibodies specific to the other species of Chlamydia.

It is another object of the present invention to provide for a method of diagnosing Chlamydia or *C. trachomatis* infection by detection of anti-*C. trachomatis* antibodies in the body fluid of an individual using as test reagent the above-mentioned mixture of peptides.

A still further object of the present invention is to use the above mixture of peptides as a vaccine to immunize an individual against *C. trachomatis* infection by any of the serovars of *C. trachomatis.*

Other objects and aspects of the present invention will arise from the following detailed disclosure of the invention.

The term "body fluid", as used herein, comprises fluids sampled from within the body, such as blood or lymph, local secretions, such as tears, semen, urine, sweat, sputum etc., samples obtained by washing (e.g. bronchiolar lavage) or swabbing, including cervical smears, and the like.

The term "peptide", as used herein, comprises peptides obtained by chemical synthesis, or by cleavage, either by chemical means or by using proteolytic enzymes, of a larger peptide or protein.

DESCRIPTION OF THE PREFERRED EMBODIMENTS

In the following detailed disclosure of the invention, there will be provided, amongst other details, the amino acid sequences of the various peptides constituting the mixture of peptides in accordance with the present invention. These sequences will be written in the form of the single letter amino acid code. For the purposes of clarity, the following is the key to this single letter code:

| Single Letter Code | Three Letter Code | Full name of Amino Acid |
|---|---|---|
| A | Ala | alanine |
| C | Cys | cysteine |
| D | Asp | aspartate |
| E | Glu | glutamate |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

Further, as will be appreciated by all skilled artisans, the sequences of the peptides in accordance with the present invention have been derived from the known and published *C. trachomatis* MOMP amino acid sequence which has been elucidated for all the various *C. trachomatis* serovars. For example, the above-noted EP 0 192 033 provides the full sequence of MOMP, the above EP 0 348 725 provides the sequences of various MOMP-derived peptides and the above WO 94/06827 provides the sequences of MOMP-derived peptides from the various *C. trachomatis* serovars. In these publications, reference is also made to a number of other publications in which the full sequences of MOMP from various serovars has been published. Hence, all of the aforesaid publications and relevant publications indicated therein are included in the present specification in their entirety as concerns the known sequences of MOMP from all the *C. trachomatis* serovars.

The present invention is based on the finding that by modifying certain specific peptides derived from the second and fourth variable domains of the immunodominant MOMP protein of *C. trachomatis* and preparing a mixture of such peptides it is possible to obtain a mixture of such peptides that is highly specific to anti-MOMP antibodies specific to the MOMP of *C. trachoniatis* and which has no cross-reactivity with anti-MOMP antibodies specific to the MOMP of other Chlamydia species such as *C. pneumoniae* or *C. psittaci*. Further, it has also been found in accordance with the present invention that by using such a mixture of peptides in a kit for the diagnosis of *C. trachomatis* disease, there is provided a kit having very high sensitivity and very high specificity towards IgA or IgG antibodies specific for *C. trachomatis* MOMP when present in a test body fluid sample assayed with this kit.

Accordingly, the present invention provides a mixture of peptides derived from the variable domains of the *Chlamydia trachomatis* (*C. trachomatis* ) immunodominant major outer membrane protein (MOMP), said mixture characterized by having specificity only to *C. trachomatis* anti-MOMP antibodies and being non-cross reactive with anti-MOMP antibodies of other Chlamydia species and said mixture also characterized by having specificity to anti-MOMP antibodies from all serovars of *C. trachomatis*, said mixture of peptides comprising about 4 peptides being selected from the group of peptides consisting of:

(a) SEQ ID NO. 1, herein also designated peptide 4A, having the amino acid sequence:

IFDTTLNPTIAGAGDVK;

(b) SEQ ID NO. 2, herein also designated peptide 4B having the amino acid sequence:

VDITTLNPTIAGCGSVAK;

(c) SEQ. ID NO. 3, herein also designated peptide 4C, having the amino acid sequence:

CVFDVTTLNPTIAGAGDVK;

(d) SEQ. ID NO. 4, herein also designated peptide 4D, having the amino acid sequence:

LAEAILDVTTLNPTITGKAVVSK;

wherein all of said peptides (a)–(d) are derived from the fourth variable domain (VDIV) of said MOMP;

(e) SEQ. ID NO. 5, herein also designated peptide *C.t*2A having the amino acid sequence:

CDNENQSTVKTNSVPNMSLDQSK, wherein said peptide (e) is derived from the second variable domain (VDII) of said MOMP;

(f) SEQ. ID NO. 6, herein also designated as *C.t* VDI, having the amino acid sequence:

VAGLENDPTTNVARA;

(g) SEQ. ID NO. 7, herein also designated as *C.t* VDII, having the amino acid sequence:

DNENNATVSDSKLVPNHMSDQS;

(h) SEQ. ID NO. 8, herein also designated as *C.t* VDIV, having the amino acid sequence:

LDVTTNATIAGKGTVV;

(i) analogs of any one of peptides (a)–(h), wherein said analogs have essentially the same biological activity as said peptides (a)–(h), said analogs having between about 9 to about 35 amino acid residues and differing from said peptides (a)–(h) by having one or more additions, deletions or substitutions, or by being combinations of an N-terminal part of one peptide selected from (a) to (d) or (h) with a C-terminal part of another peptide selected from (a) to (d) or (h), such that the complete sequence will be homologous to the VDIV sequence, or by being combinations of an N terminal part of one peptide selected from (e) or (g) with a C-terminal part of another peptide selected from (e) or (g), such that the complete sequence will be homologous to the VDII sequence.

Preferred mixtures in accordance with the invention are:

A mixture of peptides, wherein the peptides are analogs of peptides (a) to (h), and wherein all of said analogs are chosen to correspond to a MOMP VD sequence of one or more of the groups of serovars.

A mixture of peptides as defined above, characterized in that the mixture has specificity to a single serovar or group of serovars of *C. trachomatis* only.

A mixture of peptides, said mixture characterized by having specificity to anti-MOMP antibodies from all serovars of *C. trachomatis.*

Preferred mixtures of peptides in accordance with the present invention having specificity to anti-MOMP antibodies from all serovars of *C. trachomatis* are:

A mixture of peptides noted above being a mixture of 4 peptides (a), (b), (c) and (d), or a mixture of one or more of said peptides (a)–(d) with one or more analogs of (a)–(d), wherein, when said mixture contains 4 peptides selected from any of the possible combinations of (a) or analog of (a)+(b) or analog of (b)+(c) or analog of (c)+(d) or analog of (d);

A mixture of peptides as noted above being a mixture of 4 peptides (a), (b), (c) and (e), or a mixture of one or more of said peptides (a)–(c) and (e) with one or more analogs of (a)–(c) and (e), wherein, when said peptides and said analogs constitute said mixture, the mixture contains 4 peptides selected from any of the possible combinations of (a) or analog of (a)+(b) or analog of (b)+(c) or analog of (c)+(e) or analog of (e);

A mixture of peptides as noted above being a mixture of said peptides (a), (b), (c) and (d), wherein said peptides are present in said mixture in equal amounts;

A mixture of peptides as noted above being a mixture of said peptides (a), (b), (c) and (e), wherein said peptides are present in said mixture in equal amounts.

The present invention also provides the said peptides conjugated directly or indirectly (e.g., via beads and/or linkers) to a detectable marker, such as, for example, a radioactive label, an enzyme, avidin or a derivative thereof, biotin, digoxygenin, gold, ligands, haptens, metals or metal compounds having magnetic properties, and the like.

The present invention also provides a kit for the diagnosis of *C. trachomatis* infection comprising any of the above mixtures of peptides and manufacturer's instructions for use of said kit.

Preferred kits according to the invention are selected from RIA, EIA, ELISA, Immuno competition assays, lateral chromatography assays, and the SeroRapid® assay.

A particularly preferred kit according to the present invention is a kit carrying out an enzyme linked immunoassay (ELISA), and said kit comprises said mixture of peptides immobilized on a solid support and the reagents for performing said ELISA.

Likewise, the present invention also provides for the use of any of the above mixtures of peptides for the preparation of a diagnostic kit for the detection of *C. trachomatis* infection.

Furthermore, the present invention also provides for a method for detecting *C. trachomatis* infection in an individual comprising:

(a) obtaining a body fluid sample from said individual;

(b) contacting said body fluid sample with any of the above mixtures of peptides under suitable assay conditions; and (c) determining the extent of reaction between said body fluid sample and said mixture of peptides.

Preferred body fluid samples are serum, saliva, tear fluid, urine, semen, cervical smears, bronchiolar lavage and sputum.

A preferred method of the present invention is a method comprising performing a diagnostic assay of the ELISA type, wherein said mixture of peptides is immobilized on a solid support, and then contacted under suitable ELISA conditions with said body fluid sample and wherein if said body fluid sample contains antibodies specific for *C. trachomatis* MOMP, there will be a detectable positive reaction with said mixture of peptides.

Preferred body fluids for diagnosis are serum, saliva, urine and tear fluid. Serum is particularly preferred.

Further, the present invention provides for the use of the said peptides for the purpose of vaccination. The mixture of the peptides may be used in order to achieve immunization against all strains of *C. trachomatis*, while single peptides may be used in order to achieve immunization against groups of *C. trachomatis* serovars, like e.g., the group consisting of serovars A–C, or D–K, or of the different L serovars.

Other aspects and embodiments of the present invention will be set forth in the following detailed description of the invention or will clearly arise therefrom.

BRIEF DESCRIPTION OF THE DRAWINGS

In the following Figures, the reactivity of the sera to anti-Chlamydia antibodies (positive or negative) was characterized by Microimmunofluorescence, MIF, unless indicated otherwise.

FIG. 1 shows the specificity of the test antigens towards serum obtained from a positively identified *C. trachomatis*-infected individual, as described in Example 1. Open bars, negative sera, filled bars, positive sera.

FIG. 2 shows the specificity of the test antigens towards serum obtained from a positively identified *C. pneumoniae*-infected individual, as described in Example 1. Open bars, negative sera, filled bars, positive sera.

FIG. 3 shows the specificity of the test antigens, or of the indicated combinations thereof, towards serum obtained from a positively identified *C. trachomatis* and *C. pneumoniae*-infected individual, as described in Example 1. Open bars, negative sera, filled bars, positive sera.

FIG. 4 shows the relative sensitivity and antigenicity of the test antigens towards sera obtained from various infected individuals, as described in Example 1. N, Number of sera tested; A, Total number of sera identified positively by MIF; B, total number of sera identified positively by peptide system.

DETAILED DESCRIPTION OF THE INVENTION

Figure 1:
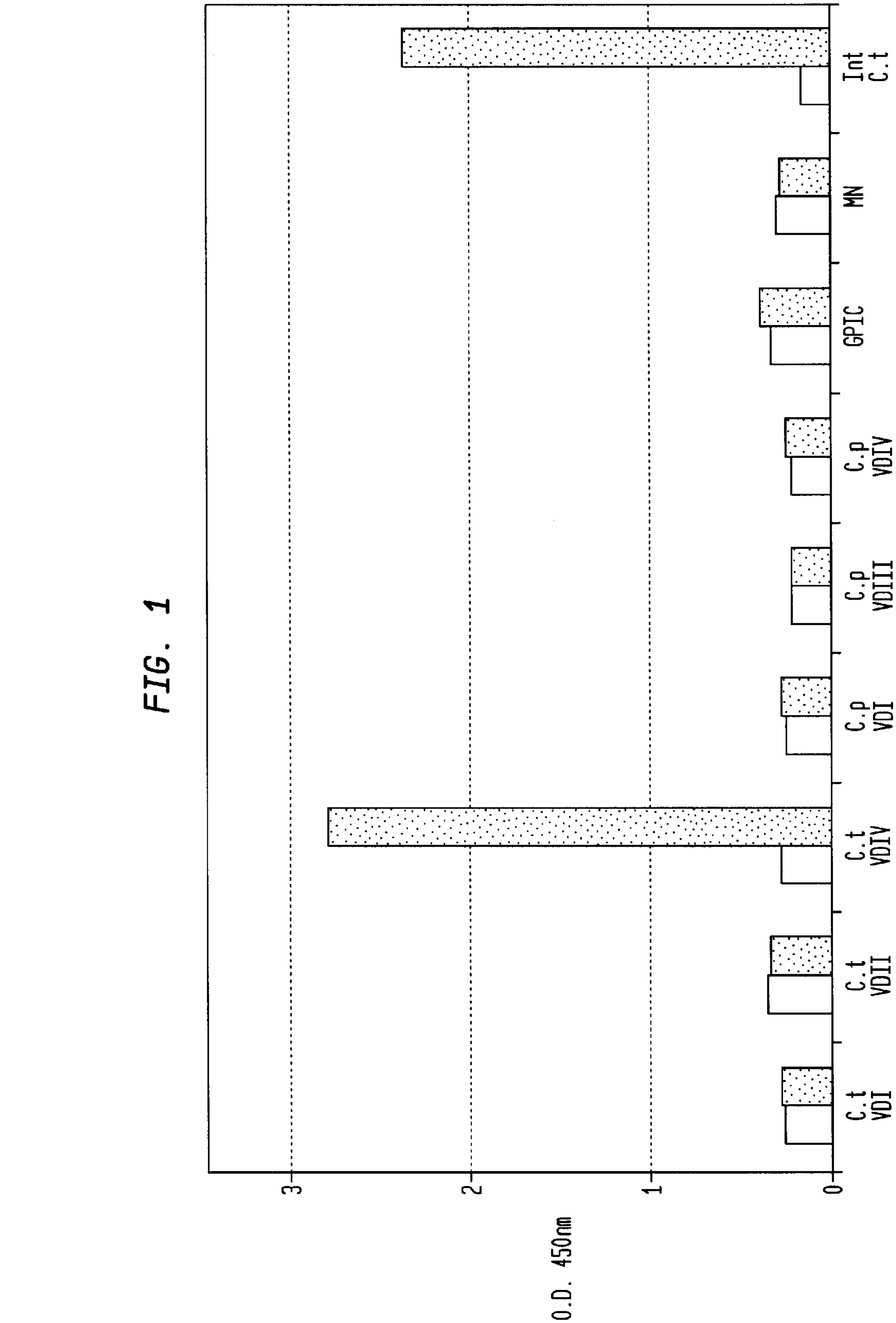
FIGS. 1–4 are bar graph representations of the results showing the reactivity of various test antigens, i.e., peptides derived from *C. trachomatis* (*C.t.*), *C. pneumoniae* (*C.p.*), and *C. psittaci* (CPIC) MOMP, *C. trachomatis* elementary bodies (MN), or intact Chlamydia antigen (Int.C.t.) towards various test sera.

The present invention concerns a new mixture of peptides derived from the second and fourth variable domains of the *C. trachomatis* MOMP and the use of such a mixture of peptides in diagnostic kits to detect *C. trachomatis* infection in an individual, specifically by detecting the presence of anti-*C. trachomatis* MOMP antibodies in test serum samples. The aforesaid mixture of peptides has revealed a heretofore not described high specificity towards anti-*C. trachomatis* MOMP antibodies and also an essentially complete absence of any cross reactivity with anti-MOMP antibodies of other Chlamydia species. Hence, the present invention also provides a highly sensitive and highly specific kit for the diagnosis of *C. trachomatis* infection, which kit is based on the above mixture of peptides.

Preferred kits in accordance with the present invention are those based on ELISA technology as are detailed herein below, and which contain the usual ELISA reagents, or more preferably, various of these reagents which have been improved to provide kits with very high sensitivity, long shelf life and ease of use.

As regards the various peptides which may be used in accordance with the present invention, the five newly synthesized peptides herein designated 4A, 4B, 4C, 4D and *C.t*2A have been shown to be most preferable for the detection of anti-MOMP antibodies specific to *C. trachomatis* in a serum sample. These peptides are most suitable for detecting the aforesaid antibodies of the IgA or the IgG type. The specific sequences of these five new peptides have been set forth hereinabove and below. It is to be understood by all of skill in the art that suitable analogs of these new peptides may be readily synthesized by now-standard peptide synthesis methods and apparatus. The only limitation on such analogs is that they have essentially the same high specificity to anti-*C. trachomatis* MOMP antibodies and the same essentially zero cross reactivity with anti-MOMP antibodies of other Chlamydia species. All such analogs will essentially be based on the new peptides as regards their amino acid sequence but will have one or more amino acid residues deleted, substituted or added. When amino acid residues are substituted, such substitutions which are envisaged are those which do not significantly alter the structure or biological activity of the peptide, for example basic amino acids will be replaced with other basic amino acids, acidic ones with acidic ones and neutral ones with neutral ones. The overall length of the analog peptide will be between about 9 to 35 amino acids. Preferably, when amino acid residues are deleted, the same above restraints are applied as regards obtaining the aforesaid biologically active peptides, and also wherein such deletion analogs will still have between about 17 to about 23 amino acid residues (deletion analogs will usually be no less than about 13 amino acid residues in length). Further preferably, when amino acid residues are added, the aforesaid restraints concerning biological activity are applied and such addition analogs will usually still have between about 17 to about 23 amino acids (addition analogs will usually be up to about 30 amino acids in length).

For the production of the peptides and the kits containing them in accordance with the present invention, well known standard methods of peptide synthesis have been utilized, and the kits are generally based on ones for carrying out assays of the ELISA type and thus contain besides the peptides various other standard ELISA reagents. With each such kit of the invention, detailed instructions are provided for operation of the ELISA procedure as well as various warnings and other precautions necessary. In accordance with the present invention, there are also provided various improved reagents for incorporation into the kits, as mentioned above, and as detailed below.

It should be appreciated that the new peptides, and in particular, the new mixtures thereof in accordance with the present invention, may be used in various other forms of diagnostic assays to detect *C. trachomatis* infection, the use not being limited only to assays of the ELISA type. Many such assays have been developed, for example, the MIF assays. Likewise, the kits of the present invention may be designed for carrying out diagnostic assays based on these other assay techniques and are hence not limited only to kits for performing such ELISA assays.

The present invention will now be described in more detail in the following non-limiting examples and their accompanying figures.

EXAMPLE 1

Development of a Mixture of MOMP-derived Peptides Specific for all Serovars of *C. trachomatis* Having no Cross-reactivity With MOMP From Other Chlamydia Species As noted above, one aim of the present invention was to develop a peptide-based diagnostic kit that will distinguish serologically between the three Chlamydia species. A series of experiments were carried out for optimizing the peptide-based ELISA assay, as well as stabilizing the kit. The peptide-based ELISA technology will be described in more detail herein below.

The first research step included the synthesis of three species-specific *Chlamydia trachomatis* (also designated in short herein below as "*C.t*") peptides and three of *C. pneumoniae* (also designated in short herein below as "*C.p*") species specific peptides. These peptides originated from the four variable domains (VDI–VDIV) of Chlamydia immunodominant major outer membrane protein (MOMP), as described for *C. trachomatis* MOMP in the above Yuan et al., 1989, and for *C. pneumnoniae* MOMP in Melgosa et al., Infect. Immun. 59, p. 2195–2199 (1991).

Three peptides originated from *C. trachomatis* MOMP protein and are designated herein as:

A. SEQ. ID NO. 6, herein also designated as *C.t* VDI, having the sequence:

VAGLENDPTTNVARA;

B. SEQ. ID NO. 7, herein also designated as *C.t* VDII, having the sequence:

DNENNATVSDSKLVPNHMSDQS;

C. SEQ. ID NO. 8, herein also designated as *C.t* VDIV, having the sequence:

LDVTTNATIAGKGTVV;

Three peptides originated from *C. pneumoniae* MOMP protein, and are designated herein as:

D. SEQ. ID NO. 9, herein also designated as *C.p* VDI, having the sequence:

NYTTAVDRPN;

E. SEQ. ID NO. 10, herein also designated as *C.p* VDIII, having the sequence:

AFPLPTDAGVATATGTKS;

F. SEQ. ID NO. 11, herein also designated as *C.p* VDIV, having the sequence:

SLLGNALSTTDSFSDFMQIV. The amino acids TA in position 7 in the corresponding sequence of the above Melgosa et al. were deleted.

The above peptides, as well as all the peptides synthesized and used in accordance with the present invention, were synthesized using standard peptide synthesis methods and apparatus, now well known in the art. The peptides were analyzed by HPLC and had about 80–90% purity, and were formulated as stable lyophilized powders.

To determine whether or not these peptides can bind specifically to Chlanrydia-infected human sera, the present analysis was first focused on calibrating the peptide diagnostic system by an ELISA methodology.

It should be noted that the aforesaid ELISA methodology used to calibrate the peptide diagnostic system is a standard well known methodology of which all of skill in the art are aware, and which has been published in many articles, patents and standard texts of the art. More details of this technology where specifically relevant to the present invention are provided in the following examples concerning the kits of the present invention.

In another set of experiments, Chlamydia species-specific human sera were tested for their ability, specifically the IgG antibodies in these sera, to bind specifically Chlarnydia species-specific peptides using the peptide-based diagnosis system described above. In these experiments, each row of wells of multiwell from the microtiter plates (the solid support) were coated with a different peptide and as a control, one row of wells was coated with intact Chlamydia antigen obtained from Dr. Cavenini, Dept. of Microbiology, University of Bologna, Italy, for known anti-Chlamydia MOMP antibodies.

The results of these studies are presented in FIGS. 1–4, described briefly above.

FIG. 1 summarizes the binding pattern (dark bars) of a typical human serum from an individual infected with *C. trachomatis*. This serum binds specifically to *C.t* VDIV peptide only. Binding was observed also with the intact *C. trachomatis* antigen (Int. *C.t*). Low background binding (open or light bars) was observed, as was determined in the non-infected human serum.

Figure 2:
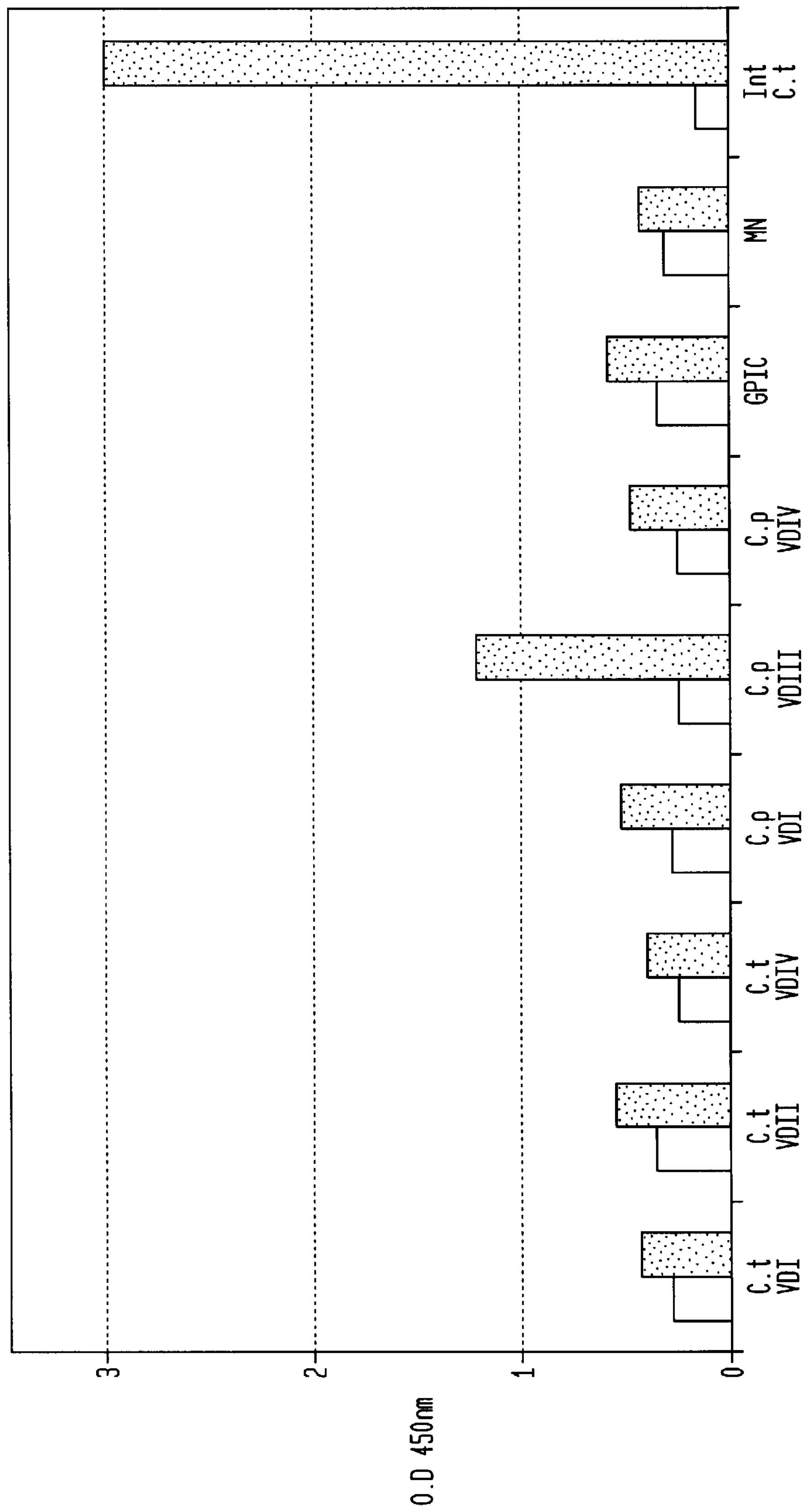
Figure 4:
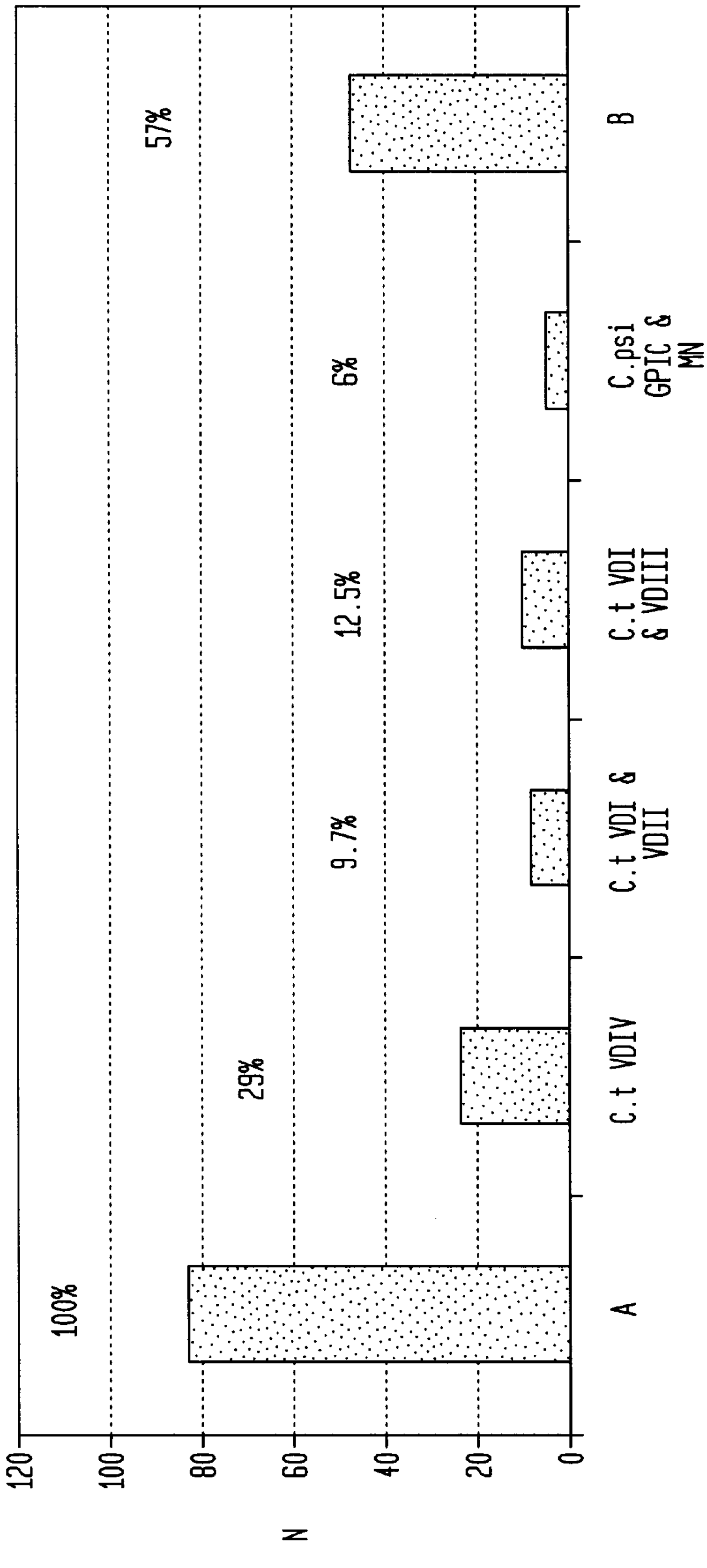

In the case of *C. pneumoniae* infected human sera, the results of which are summarized in FIG. 2, part of the infected sera bind specifically to *C.p* VDH peptide, yet with a low binding level, and part of them bind specifically to *C.p* VDI (see also the summary in FIG. 4).

Figure 3:
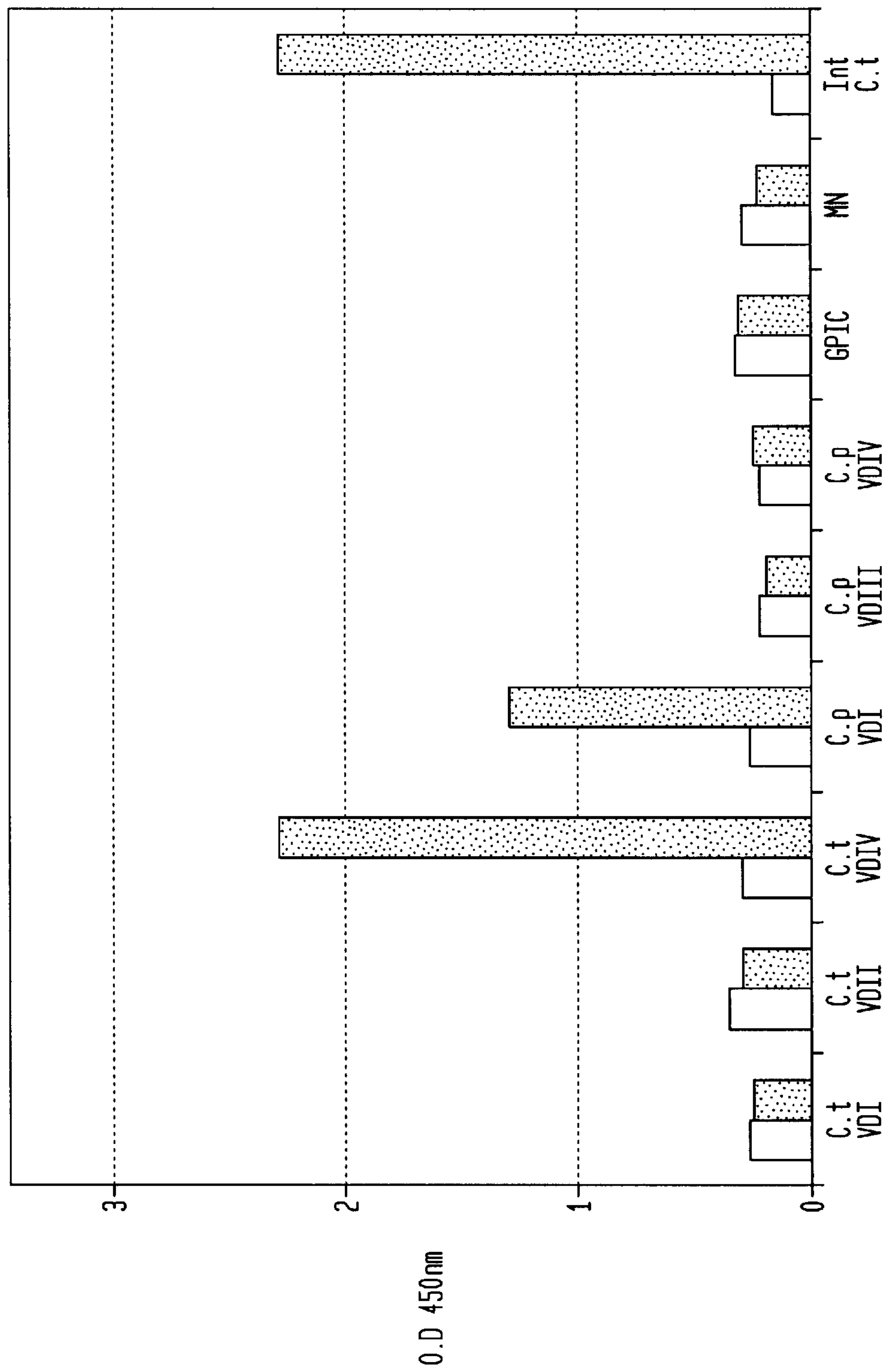

Since most of the population has had a previous infection with *C. pneumoniae*, it could also be detected in this system sera that reacted specifically with both *C. trachomatis* peptide and *C. pneumoniae* peptide, these results being summarized in FIG. 3.

FIG. 4 summarizes the sensitivity of the peptide-based diagnostic system, as well as the antigenicity of the tested peptides. From 82 Chlamydia-infected human sera tested by either the above ELISA test ("SeroELISA Chlamydia") or by a standard Microimmunofluorescence methodology (MIF), 29% reacted only with *C.t* VDIV peptide, 9.7% reacted with either *C.t* VDI and/or *C.t* VDII peptides. The total peptide system sensitivity was only 57%.

To conclude, the above results indicate that the major specific antigen for *C. trachomatis* is the *C.t* VDIV peptide, and the minor specific antigen for *C. trachomatis* is the *C.t* VDII peptide, while for *C. pneumoniae*, the major antigens are *C.p* VDI & VDII. Lack of sensitivity was observed in the peptide-based diagnostic system, as 43% of the tested sera were not detected by this system. Also, low binding activity was observed. These results therefore also reflect the above-mentioned drawbacks of the prior art peptides and their use in immunoassays to detect anti-*C. trachomatis* MOMP antibodies. Therefore, a second set of new, modified *C. trachomatis* species-specific peptides were synthesized as above using standard peptide synthesis methodology and apparatus. These peptides were derived from *C.t* VDIV sequences of different *C. trachomatis* serovars with small modifications, as indicated below. All the peptides share the *C. trachomatis C.t* VDIV core sequence (marked in italics in the following sequences), yet without any cross-homology to either *C. pneumoniae* or *C. psittaci* (as determined by comparing these peptide sequences to the known *C. pneumoniae* and *C. psittaci* sequences):

1. SEQ. 1D NO. 1, IFDXTTLNPTIAGAGDVK—In this peptide, either V (serovars B, Ba) or T (serovars D, E, L1) was deleted in the position that was marked as X. This peptide is also designated herein as C.t.4A.
2. SEQ. ID NO. 2, VDITTLNPTIAGCGSVAK—K was added at the C-terminal (originating from F and G serovars). This peptide is also designated herein as *C.t*.4B.
3. SEQ. ID NO. 3, CVFDVTTLNPTIAGAGDVK—To the sequence originating from the L2 serovar, C was added at the N-terminal and K was added at the C-terminal. This peptide is also designated herein as *C.t*.4C.

In addition to the above three new modified peptides derived from the *C.t* VDIV peptide, a fourth peptide being a new modified peptide was also synthesized having a sequence derived from the *C.t* VDII peptide:

4. SEQ. ID NO. 5, CDNENQSTVKTNSVPNMSLDQSK—Derived from the variable domain II of serovar E. C was added at the N-terminal and K was added at the C-terminal. This peptide is also designated herein as *C.t*. 2A.

For the purpose of determining cross-reactivity to *C. pneumoniae*-specific sequences, and also for the purpose of development of a *C. pneumoniae*-specific immunoassay, the following peptides derived from the MOMP protein of *C. pneumoniae* were designed:

1. SEQ. ID NO. 12, CFSMGAKPTGSAAANYTTAVDRPNPAYNK. Derived from the variable domain I. This peptide is also designated herein as *C.p*. 1A;
2. SEQ. ID NO. 13, VKGTTVNANELPNVSLSNGK. Derived from the variable domain R. This peptide is also designated herein as *C.p*. 2A.
3. SEQ. ID NO. 14, LNLTAWNPSLLGNATALSTTDSFK. Derived from the variable domain IV. This peptide is also designated herein as *C.p*. 4A.

In subsequent experiments, the above new peptides, as well as the aforementioned, previously prepared peptides, were tested using the same test procedure noted above. The tested peptides were:

*C.t*2A, *C.t*4A, *C.t*4B, *C.t*4C, *C.p*1A, *C.p*2A, *C.p*4A and C.p.VDIII.

Figure 5:
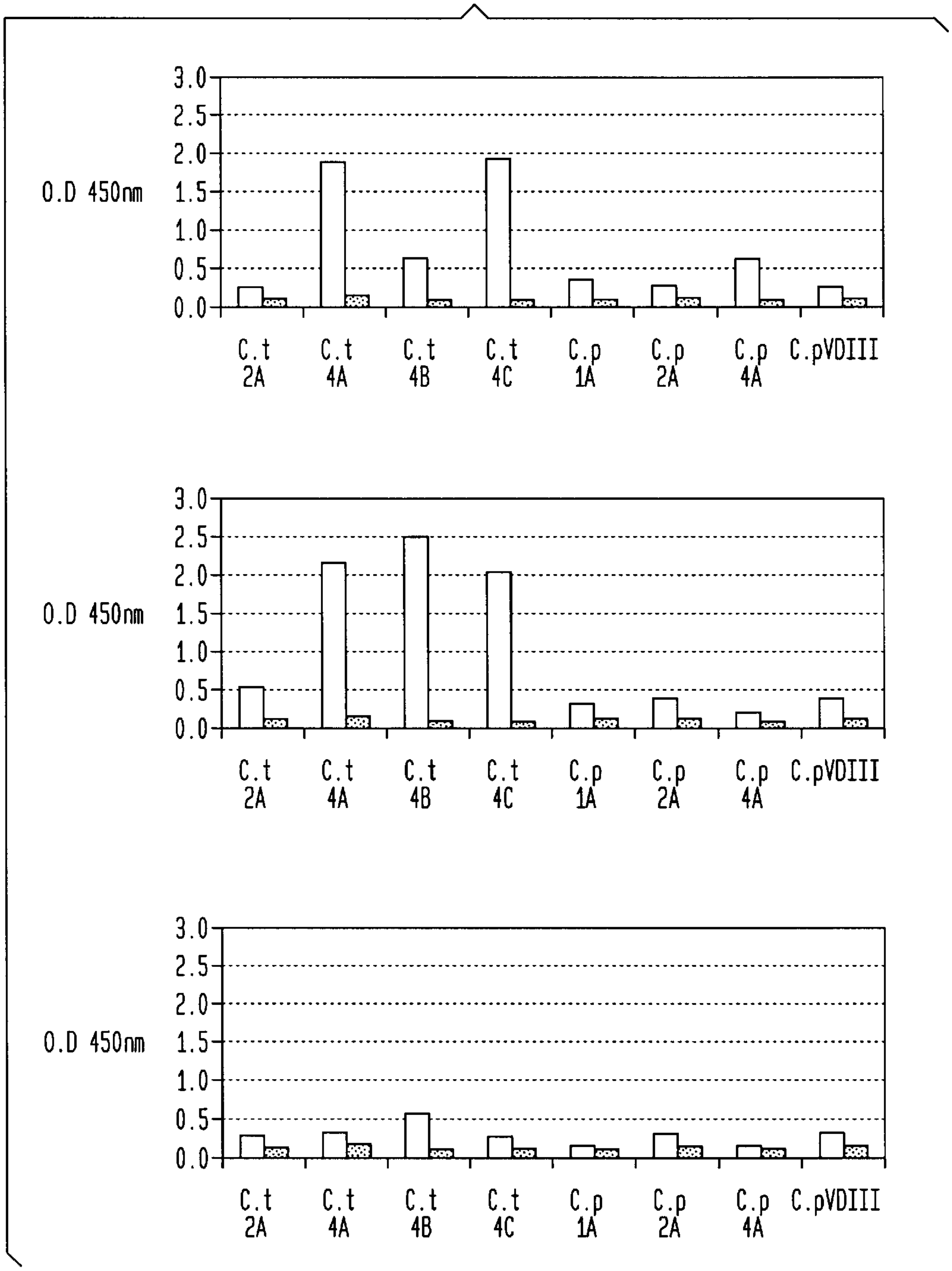
FIG. 5 shows bar graph representations of the reactivity of various new peptides synthesized in accordance with the present invention towards three different sera obtained from three different individuals positively identified as infected with *C. trachomatis*, as described in Example 1. Open bars, negative sera; filled bars, positive sera; O.D., optical density.

FIG. 5 summarizes the results of the binding of these peptides to the sera obtained from three distinct *C. trachomatis*-infected individuals. As is apparent from FIG. 5, each serum reacts with different *C.t* peptide combinations, namely, each separate bar-graph represents the results of the tests on the sera obtained from a different individual, such that the first (top) sera reacts with *C.t*4A and *C.t*4C, the second (middle) reacts with *C.t*4A, *C.t* 4B and *C.t*4C, while the third (bottom) only has some reactivity with *C.t*4B. In all cases, the open bars represent the test reactions in which the peptides were reacted with sera, while the closed (dark) bars represent the control reactions in which sera from individuals confirmed negative for Chllamydia infection (by MIF) were added to the peptides. Further, all the tested sera were apparently very specific and did not bind any of the *C.p* peptides, i.e., all the tested individuals only had anti-*C. trachomatis* antibodies.

Figure 6:
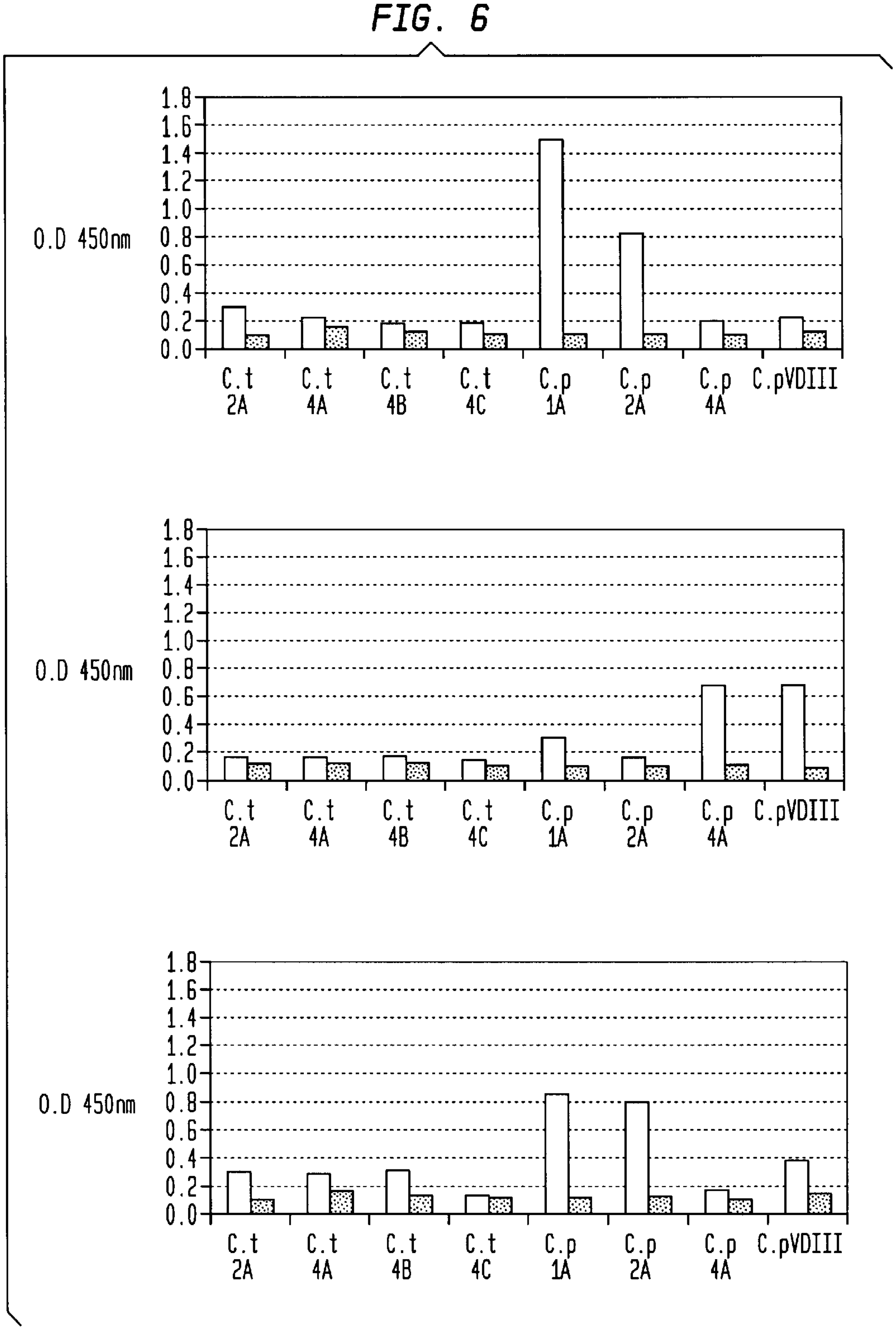
FIG. 6 shows bar graph representations of the reactivity of various new peptides synthesized in accordance with the present invention towards three different sera obtained from three different individuals positively identified as infected with *C. pneumoniae*, as described in Example 1. Open bars, negative sera, filled bars, positive sera, O.D., optical density.

Similar results were observed with *C. pneumoniae* specific sera, which are summarized in FIG. 6. As can be clearly seen, the *C. pneumoniae* sera react only with *C. pneumoniae* peptides, but not with any of the *C. trachomatis* peptides.

Figure 7:
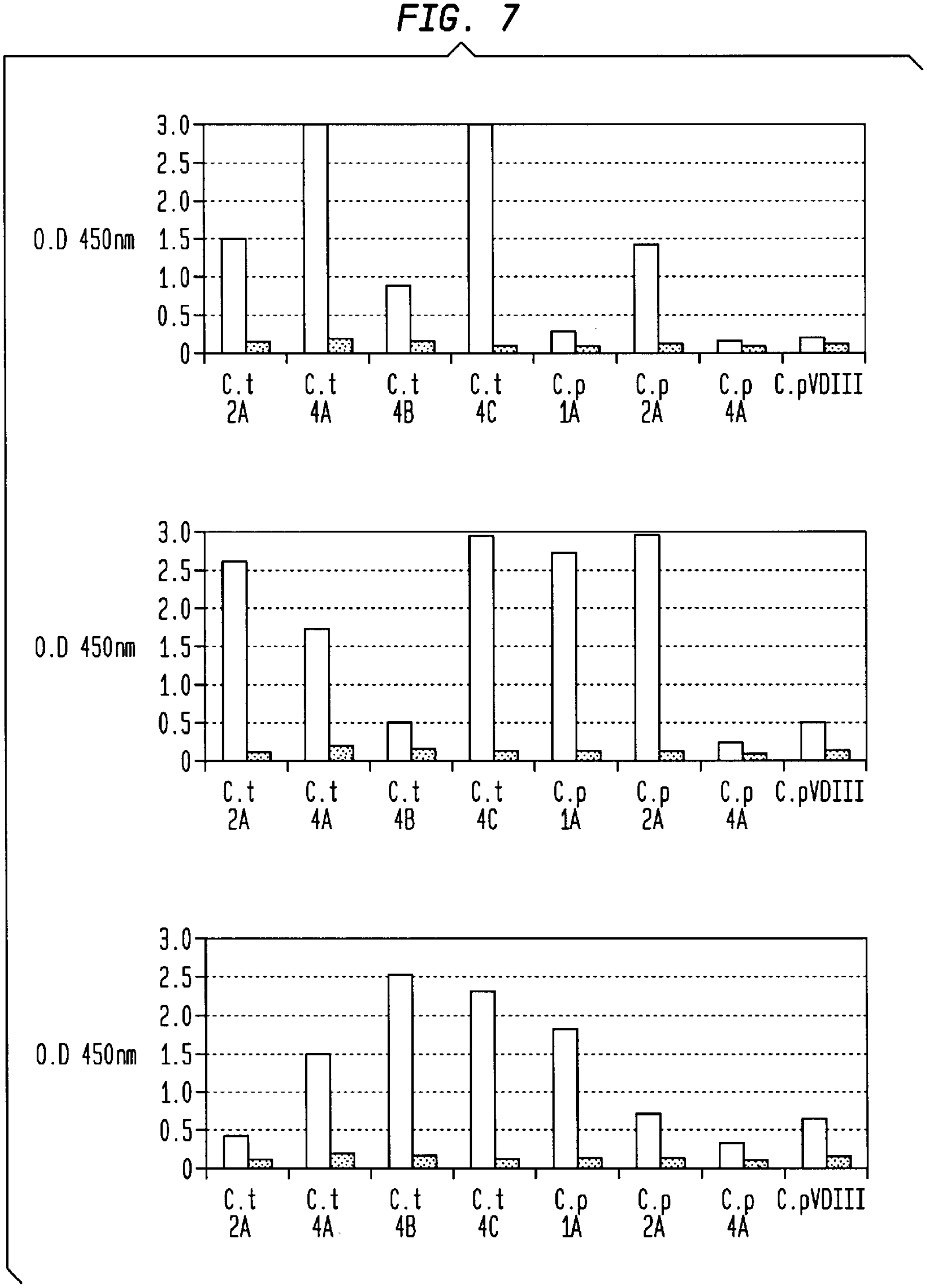
FIG. 7 shows bar graph representations of the reactivity of various new peptides synthesized in accordance with the present invention towards three different sera obtained from three different individuals positively identified as infected with *C. trachomatis* and *C. pneumoniae*, as described in Example 1. Open bars, negative sera, filled bars, positive sera, O.D., optical density.

FIG. 7 summarizes the binding pattern of three different human sera that were infected with both *C. trachomatis* and *C. pneumoniae*. Indeed, each serum interacts with both *C. trachomatis* and *C. pneumoniae* peptides, yet with altered peptide combinations, namely, the first (top) reacts with *C.t*2A, *C.t*4A, *C.t*4B, *C.t*4C and *C.p*. 2A, the second (middle) reacts with *C.t*2A, *C.t*4A, *C.t*4C, *C.p*. 1A and C.p. 2A, and the third (lower) reacts with *C.t* 4A, *C.t*4B, *C.t*4C, *C.p*. 1A, *C.p*. 2A and *C.p*.VDIII.

In another series of experiments, the sensitivity of the various above *C. trachomatis* peptides was tested on a large number of sera obtained from a number of different individuals known to have been infected with *C. trachomatis* by virtue of testing positive in tests in which these sera were reacted with *C. trachomatis* elementary antibodies containing MOMP as the major antigen. The sensitivity of the *C. trachomatis* peptide *C.t* VDIV alone, as opposed to the other *C. trachomatis* VDIV peptides, *C.t*4A, 4B and 4C, is summarized in Table I.

TABLE I

The sensitivity of C. trachomatis peptide VDIV alone as opposed to the other *C trachomatis* VDIV peptides, C.t4A, 4B, and C.t4C.

| | *C.traehomatis* EBs positive | C.t VDIV positive | Positive on C.t 4A &/or C.t 4B &/or C.t4C |
|---|---|---|---|
| *C. trachomatis* EBs positive | 53 | 18 | 48 |
| | — | 34% | 91% |

From this data, it is apparent that out of the 53 sera which were positive on *C. trachomatis* elementary bodies (EBs), only 18 reacted as positive with *C.t* VDIV peptide, while 48 reacted as positive with at least one of the new *C. trachomatis* peptides *C.t*4A, *C.t*4B and *C.t*4C. Interestingly, none of the tested sera reacted only with the *C.t* VDIV peptide, i.e., all sera reacting with *C.t* VDIV also reacted with at least one of the other peptides, indicating also that *C.t* VDIV when compared to the new peptides *C.t*4A, *C.t*4B and *C.t*4C, does not have any unique epitope not contained in the new peptides.

Figure 8:
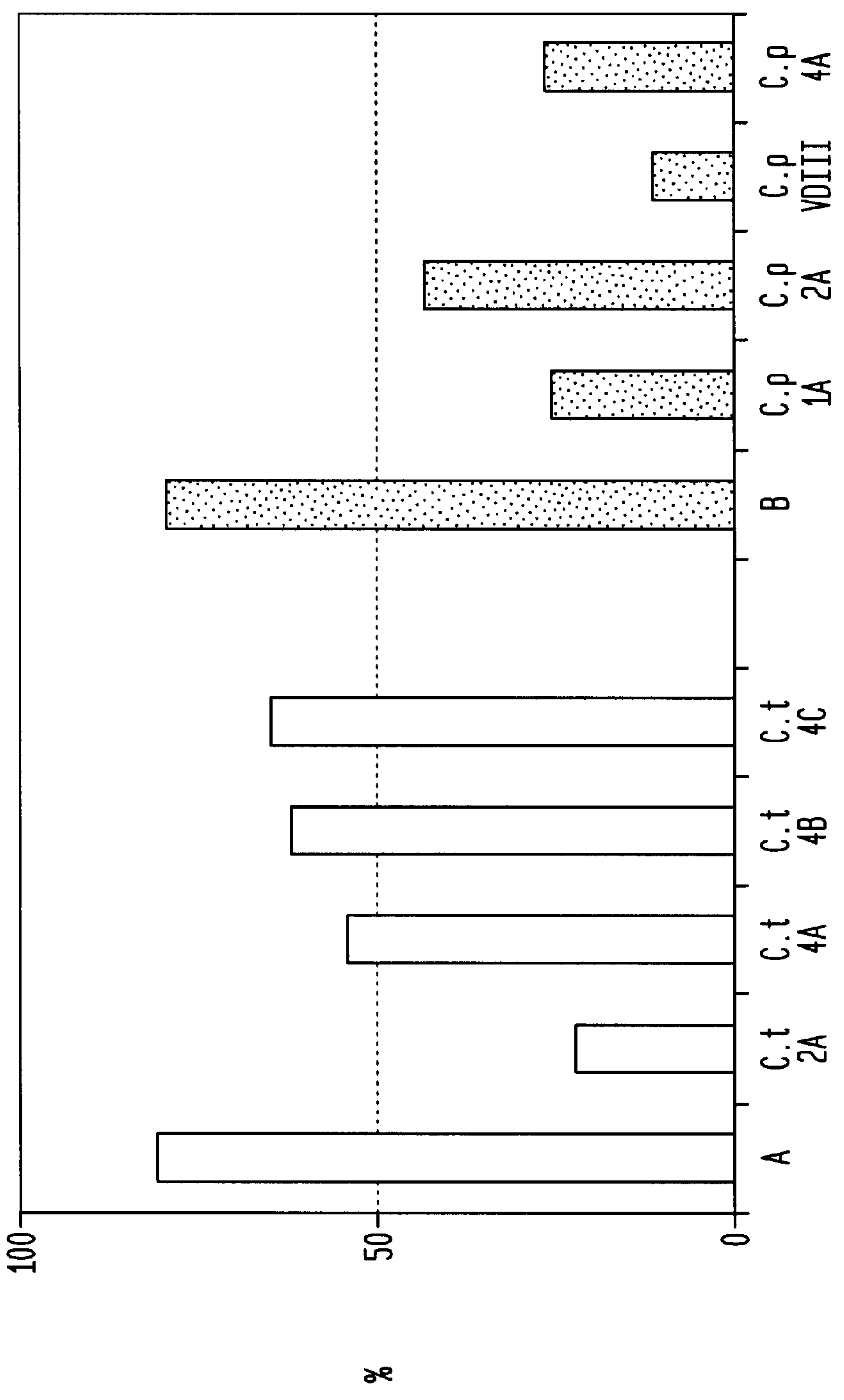
FIG. 8 is a bar graph representation of the relative diagnostic value of each of the newly synthesized peptides according to the present invention towards anti-MOMP antibodies present in test sera, as described in Example 1. Open bars, *C.trachomatis*-positive sera, filled bars, *C.p.*-positive sera, %, percent of the total positive (by MIF) sera. *C.t.*, total positive (by peptide system) for *C. trachomatis; C.p.*, total positive (by peptide system) for *C. pneumoniae.*

The diagnostic value of each peptide (*C.t*4A, *C.t*4B, *C.t*4C and *C.t*2A) was determined, the results of which are summarized in FIG. 8. Out of 81 *C. trachomatis* IgG positive human sera assayed by the *C. trachomatis* peptide-based ELISA assay, only 22 were positive to *C.t*2A, 54 were positive to *C.t*4A, 62 were positive to *C.t*4B, and 65 were positive to *C.t*4C.

Figure 9:
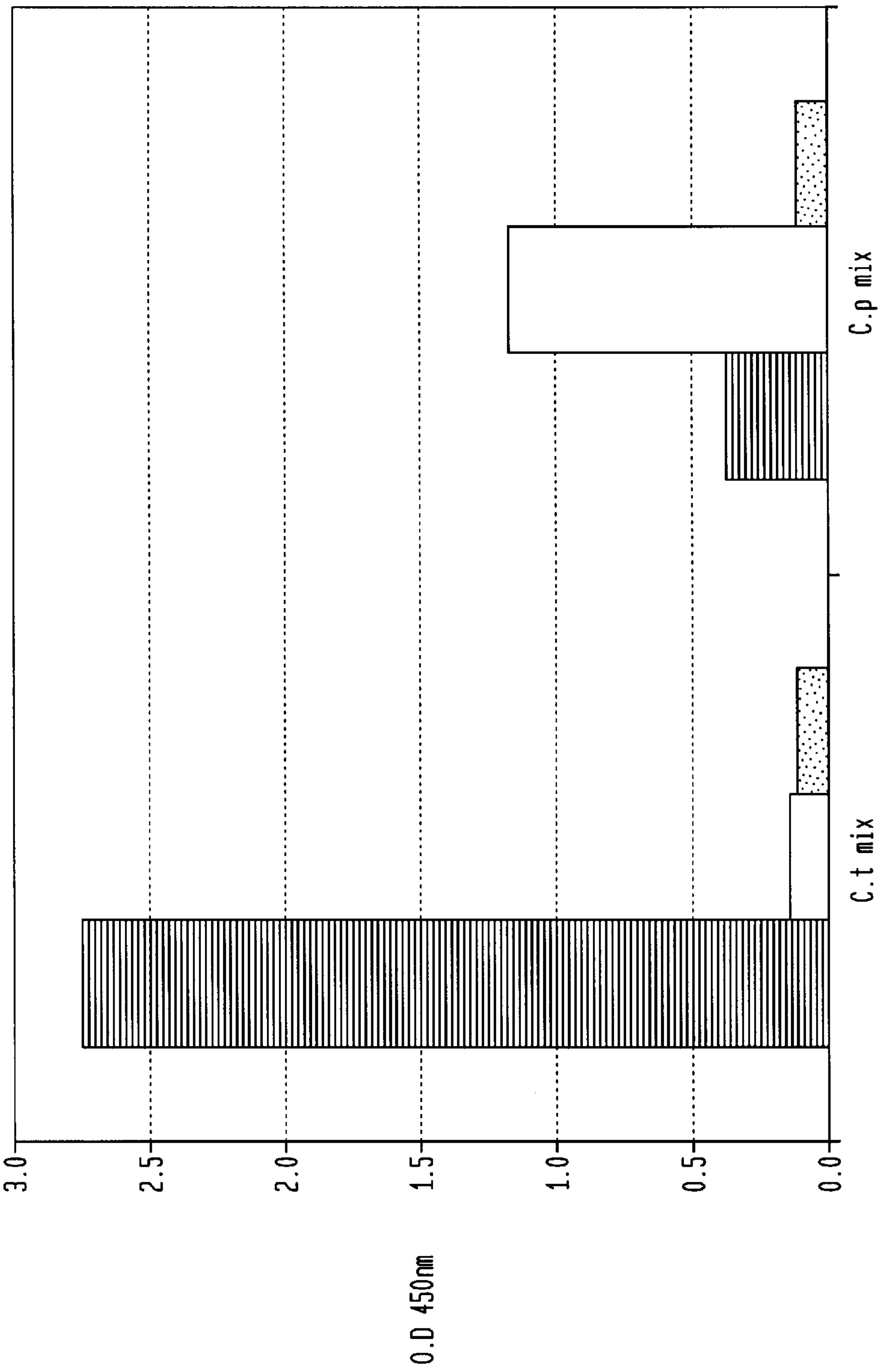
FIG. 9 is a bar graph representation of the results showing the specificity and reactivity of mixtures of new peptides of the invention towards serum obtained from positively infected individuals, as described in Example 1. *C.t* mix, mixture of peptides specific for *C. trachomatis; C.p* mix, mixture of peptides specific for *C. pneumoniae*, hatched bars, *C.t* positive serum, open bars, negative serum, filled bars, *C.p* serum, O.D., optical density.

Since all the *C. trachomatis* peptides contribute significantly to the diagnostic value, the reactivity of *C. trachomatis* specific sera was tested also on a mixture (1:1:1:1) of the above four new *C. trachomatis* peptides and as a control on the four above-noted *C. pneumoniae* peptides. These results are summarized in FIG. 9, from which it is apparent that the mixture of the *C.t* peptides has a very high specific reactivity to *C. trachomatis* sera only, any cross-reactivity with *C. pneumoniae* sera being insignificant and essentially at background levels only (negative control—sera from individuals confirmed negative for Chlamydia infection (by MIF) added to peptide mix). In contrast, the *C.p*. peptide mixture has less reactivity to *C.p* sera and a significant cross-reactivity with *C.t* sera.

Upon consideration of the literature concerning the various serovars of *C. trachomatis*, it seems that the three new *C. trachomatis* peptides (4A, 4B and 4C) can cover only the B complex serovars (serovars B, D and E) and the intermediate complex serovars (serovars F and G). However, the prevalence of C complex serovars (serovars C, H, I, J, K) is between 10–20% in different countries. Therefore, the following new peptide, which is derived from a peptide of complex C serovars, was synthesized using standard synthesis methodology and apparatus as noted above. This peptide is also from the *C.t* VDIV region as with new peptides 4A, 4B and 4C.

This new peptide is:

5. SEQ. ID NO.4, LAEAILDVTFTLNPTITGK XAVVSK—This peptide is also designated herein as 4D. This sequence is derived from the K serovar (a C complex serovar), G was deleted in the position marked as X and K was added at the C-terminal. This peptide also has the *C.t* VDIV core sequence TTLNPTIT indicated in italics above.

In another set of examples, the peptides *C.t*2A, 4A, 4B, 4C and 4D were tested on sera from patients scheduled for in-vitro-fertilization (IVF) for IgG reactivity. 27 such sera reacted positively with at least one *C. trachomatis* peptide. Out of the 27, 20 were positive to *C.t*4D. Interestingly, however, out of these 20 sera 4 were positive exclusively to *C.t*4D. Further, of the other 23 sera (which did not react exclusively with *C.t*4D), 5 were exclusively positive to *C.t*4B. These results clearly indicate the necessity of these two peptides *C.t*4B and *C.t*4D for increasing the sensitivity of the new peptides, especially a mixture thereof, to sera from all the *C. trachomatis* serovars. These results also indicate that these two peptides, *C.t*4B and *C.t*4D, possibly also define serovar-specific epitopes. These results are summarized in Table II below.

TABLE II

The sensitivity of *C. trachomatis* peptides on IVF sera

| Positive IVF sera on at least one *C. trachomatis* peptide | No. of positive sera on each peptide C.t 2A | C.t 4A | C.t 4B | C.t 4C | C.t 4D |
|---|---|---|---|---|---|
| 27 | 4 | 17 | 23 | 18 | 20 |
| % positive out of 27 | | | | | |
| — | 15 | 63 | 88 | 67 | 74 |

The sensitivity of different *C. trachomatis* mixtures was also tested, and the results are summarized in Table III. MIX 1 consisted of equal amounts of the *C.t*2A, 4A, 4B and 4C peptides, whereas MIX 2 consisted of equal amounts of the *C.t*4A, 4B, 4C and 4D peptides. Considering the results of immunoassays using these two mixtures, which are summarized in Table III, it is clear that MIX 2 has the best sensitivity to *C. trachomatis* antibodies (as present in the sera tested).

TABLE III

The sensitivity of different mixtures of *C. trachomatis* peptides

| | No. of positive sera out of 29 MIX 1* | MIX 2** |
|---|---|---|
| | 21 | 26 |
| % out of 29 positive sera | 72 | 90 |

*MIX 1-C.t 2A, 4A, 4B, 4C
**MIX 2-4A, 4B, 4C, 4D

Based on this and other studies (results not shown), it was decided that the most preferred mixture for use in a diagnostic kit will be MIX 2. Such a mixture provides highest sensitivity to anti-*C. trachomatis* antibodies (anti-MOMP antibodies) present in all sera tested so far, as well as the lowest (negligible and equal to background levels only) cross-reactivity with antibodies in sera from individuals positively infected with other Chlamydia species.

It should be noted that as regards the above new peptide *C.t*4C, experimental results (not shown) revealed that the C amino acid residue was very important for its sensitivity, removal of this C residue (or synthesis of the peptide without C at the N-terminus) caused a drop of about 55% in its reactivity to certain sera.

EXAMPLE 2

Conditions That Enhance Stability of Immobilized Peptides for Long-term Storage In view of the use of the peptide mixture described herein for the development of a diagnostic kit it is essential to check the immobilized peptides for stability, as they are, e.g. in the form of peptide-coated microtiter plates, to be provided as components of a kit. By employing accelerated stability tests, i.e. storing the immobilized peptides at 37÷C and comparing the test results with results obtained from peptides stored at 4÷C, it has been found that the composition of the buffer employed for blocking after adsorption of the peptides is critical. In particular, this buffer should not, in contrast to ELISA method as known in the art, contain TWEEN-20. Also, the addition of 1–20% sucrose, preferably 10% sucrose, was found to further enhance stability of the peptides for storage. As will be detailed below, the different peptides exhibit various degrees of instability, but all peptides can be stored stably when the sucrose-containing blocking buffer is used. As will be apparent to the skilled artisan when taking into account the necessity to use different peptides in order to achieve species-specificity as detailed in Example 1, such a buffer formulation is extremely useful when developing diagnostic kits based on peptides. The use of such buffer also stabilizes peptides derived from other sequences, as detailed below, namely, the *C. pneumoniae* MOMP VDI, VDII and VDIV. The use of such buffer for the purpose of carrying out an immunoassay with immobilized peptides is the subject of a copending application by the same applicants, Attorney's docket 4326/bc/97.

In order to test the influence of sucrose and TWEEN in the blocking solution on the stability of various peptides, four peptides derived from *C. trachomatis* and four peptides as well as a mixture of these derived from *C. pneumoniae* were tested independently. Testing was carried out by incubation of the immobilized peptides at 37÷C for three to ten days and the results compared to peptides which were incubated at 4÷C. The following Tables show on the right side ELISA results obtained with peptides incubated at the indicated temperatures and for the indicated times, while at the left side they give the ratio of the results obtained at 37÷C incubation versus the results obtained by 4÷C incubation. A ratio of about 1 or greater indicates that the peptide is stable when incubated at 37÷C, while lower ratios (<0.9) indicate instability of the immobilized peptide.

A) Results Obtained Using *C. trachomatis* Peptides

Tables 4–15 show the results of ELISA essays carried out with immobilized peptides stored dry for the indicated times and at the indicated temperatures. The assay was carried out as described for Table 2, with 10% sucrose and/or 0.05% TWEEN-20 added to the blocking buffer where indicated.

All of the tested *C. trachomatis* peptides were essentially stable when blocking buffer containing sucrose was used (see Tables 4, 7, 10, 13).

When sucrose was omitted from the blocking buffer, a significant decrease in reactivity to most sera was observed for peptide Ct4A and Ct4C (Tables 5 and 11), a decrease to three of the sera for Ct4B (Table 8), and a slight decrease to four sera for Ct4D (Table 14). These data show clearly that each peptide displays several epitopes, and that the reactivity of these epitopes to the antisera is influenced differentially storage of the dried immobilized peptides, but that all epitopes can be preserved when sucrose-containing buffer is used for blocking.

When sucrose was omitted from the blocking solution and TWEEN-20 was added (as is customary in ELISA procedures), the stability of some of the peptides was decreased by much, e.g. Ct4A (compare Table 6 to Table 5), and Ct4B (compare Table 9 to Table 8), while the other two peptides were less affected, but still exhibited slightly lower reactivity when TWEEN-20 was present in the blocking buffer (compare Table 12 to Table 11 and Table 15 to Table 14).

TABLE 4 peptide Ct4A, blocker with sucrose

| | | | | | 37° C./4° C. | | |
|---|---|---|---|---|---|---|---|
| serum | 4° C. | 3 day | 7 day | 10 day | 3 day | 7 day | 10 day |
| H 156 | 1.246 | 1.437 | 1.277 | 1.333 | 1.153 | 1.024 | 1.069 |
| H 171 | 0.719 | 0.791 | 0.709 | 0.742 | 1.100 | 0.985 | 1.032 |
| H 130 | 0.627 | 0.679 | 0.635 | 0.558 | 1.083 | 1.014 | 0.890 |
| H 186 | 0.687 | 0.712 | 0.678 | 0.689 | 1.036 | 0.987 | 1.003 |
| H 203 | 0.820 | 0.822 | 0.862 | 0.740 | 1.002 | 1.051 | 0.902 |
| M92 + H 163 | 0.767 | 0.737 | 0.825 | 0.745 | 0.962 | 1.076 | 0.971 |
| F 111 | 0.483 | 0.495 | 0.466 | 0.477 | 1.025 | 0.965 | 0.989 |
| F 210 | 0.402 | 0.302 | 0.245 | 0.328 | 0.752 | 0.609 | 0.816 |

TABLE 5 peptide Ct4A, blocker without sucrose with PBS.

| | | | | | 37° C./4° C. | | |
|---|---|---|---|---|---|---|---|
| serum | 4° C. | 3 day | 7 day | 10 day | 3 day | 7 day | 10 day |
| H 156 | 1.3270 | 1.1570 | 0.9535 | 0.9165 | 0.8719 | 0.7185 | 0.6907 |
| H 171 | 0.7035 | 0.6360 | 0.5885 | 0.5380 | 0.9041 | 0.8365 | 0.7647 |
| H 130 | 0.5760 | 0.4945 | 0.4295 | 0.3920 | 0.8585 | 0.7457 | 0.6806 |
| H 186 | 0.7430 | 0.6035 | 0.5590 | 0.5435 | 0.8122 | 0.7524 | 0.7315 |
| H 203 | 0.7945 | 0.6310 | 0.5980 | 0.5640 | 0.7942 | 0.7527 | 0.7099 |
| M92 + H 163 | 0.7225 | 0.5700 | 0.5420 | 0.5335 | 0.7889 | 0.7502 | 0.7384 |
| F 111 | 0.4515 | 0.5630 | 0.4790 | 0.4755 | 1.2470 | 1.0609 | 1.0532 |
| F 210 | 0.4145 | 0.3780 | 0.4045 | 0.3950 | 0.9119 | 0.9759 | 0.9530 |

TABLE 6 peptide Ct4A, blocker without sucrose with PBS-T

| | | | | | 37° C./4° C. | | |
|---|---|---|---|---|---|---|---|
| serum | 4° C. | 3 day | 7 day | 10 day | 3 day | 7 day | 10 day |
| H 156 | 1.304 | 0.800 | 0.758 | 0.698 | 0.613 | 0.581 | 0.535 |
| H 171 | 0.669 | 0.515 | 0.494 | 0.447 | 0.770 | 0.739 | 0.668 |
| H 130 | 0.561 | 0.324 | 0.316 | 0.275 | 0.577 | 0.563 | 0.490 |
| H 186 | 0.719 | 0.530 | 0.504 | 0.451 | 0.736 | 0.701 | 0.627 |

TABLE 6-continued peptide Ct4A, blocker without sucrose with PBS-T

| | | | | | 37° C./4° C. | | |
|---|---|---|---|---|---|---|---|
| serum | 4° C. | 3 day | 7 day | 10 day | 3 day | 7 day | 10 day |
| H 203 | 0.762 | 0.493 | 0.439 | 0.371 | 0.647 | 0.576 | 0.487 |
| M92 + H 163 | 0.657 | 0.454 | 0.427 | 0.374 | 0.691 | 0.650 | 0.569 |
| F 111 | 0.422 | 0.302 | 0.441 | 0.382 | 0.716 | 1.045 | 0.905 |
| F 210 | 0.377 | 0.306 | 0.271 | 0.296 | 0.813 | 0.720 | 0.786 |

TABLE 7 peptide Ct4B, blocker with sucrose

| | | | | | 37° C./4° C. | | |
|---|---|---|---|---|---|---|---|
| serum | 4° C. | 3 day | 7 day | 10 day | 3 day | 7 day | 10 day |
| H 156 | 0.298 | 0.321 | 0.319 | 0.330 | 1.077 | 1.072 | 1.109 |
| H 171 | 0.481 | 0.481 | 0.496 | 0.483 | 1.000 | 1.031 | 1.004 |
| H 130 | 0.673 | 0.683 | 0.659 | 0.599 | 1.015 | 0.979 | 0.890 |
| H 186 | 0.642 | 0.623 | 0.609 | 0.567 | 0.971 | 0.949 | 0.884 |
| H 203 | 0.526 | 0.528 | 0.538 | 0.507 | 1.004 | 1.022 | 0.963 |
| M92 + H 163 | 0.308 | 0.291 | 0.278 | 0.262 | 0.946 | 0.902 | 0.852 |
| F 111 | 0.218 | 0.265 | 0.258 | 0.254 | 1.213 | 1.181 | 1.163 |
| F 210 | 0.266 | 0.260 | 0.260 | 0.276 | 0.979 | 0.979 | 1.040 |

TABLE 8 peptide Ct4B, blocker without sucrose with PBS.

| | | | | | 37° C./4° C. | | |
|---|---|---|---|---|---|---|---|
| serum | 4° C. | 3 day | 7 day | 10 day | 3 day | 7 day | 10 day |
| H 156 | 0.267 | 0.254 | 0.248 | 0.279 | 0.953 | 0.931 | 1.047 |
| H 171 | 0.425 | 0.350 | 0.360 | 0.340 | 0.823 | 0.848 | 0.801 |
| H 130 | 0.623 | 0.499 | 0.450 | 0.431 | 0.801 | 0.722 | 0.691 |
| H 186 | 0.566 | 0.463 | 0.440 | 0.371 | 0.818 | 0.778 | 0.655 |

TABLE 8-continued

| peptide Ct4B, blocker without sucrose with PBS. | | | | | | | |
|---|---|---|---|---|---|---|---|
| | | | | | 37° C./4° C. | | |
| serum | 4° C. | 3 day | 7 day | 10 day | 3 day | 7 day | 10 day |
| H 203 | 0.483 | 0.405 | 0.368 | 0.322 | 0.839 | 0.761 | 0.667 |
| M92 + H 163 | 0.279 | 0.301 | 0.266 | 0.296 | 1.079 | 0.953 | 1.061 |
| F 111 | 0.273 | 0.257 | 0.243 | 0.271 | 0.943 | 0.892 | 0.994 |
| F 210 | 0.255 | 0.226 | 0.260 | 0.278 | 0.888 | 1.020 | 1.092 |

TABLE 9

| peptide Ct4B, blocker without sucrose with PBS-T. | | | | | | | |
|---|---|---|---|---|---|---|---|
| | | | | | 37° C./4° C. | | |
| serum | 4° C. | 3 day | 7 day | 10 day | 3 day | 7 day | 10 day |
| H 156 | 0.300 | 0.268 | 0.267 | 0.283 | 0.892 | 0.888 | 0.943 |
| H 171 | 0.464 | 0.353 | 0.352 | 0.335 | 0.760 | 0.759 | 0.721 |
| H 130 | 0.628 | 0.435 | 0.402 | 0.369 | 0.693 | 0.640 | 0.588 |
| H 186 | 0.679 | 0.481 | 0.438 | 0.401 | 0.708 | 0.645 | 0.591 |
| H 203 | 0.566 | 0.386 | 0.319 | 0.299 | 0.683 | 0.563 | 0.528 |
| M92 + H 163 | 0.285 | 0.289 | 0.277 | 0.271 | 1.016 | 0.972 | 0.951 |
| F 111 | 0.253 | 0.243 | 0.251 | 0.254 | 0.960 | 0.990 | 1.002 |
| F 210 | 0.427 | 0.241 | 0.245 | 0.275 | 0.564 | 0.574 | 0.643 |

TABLE 10

| peptide Ct4C, blocker with sucrose | | | | | | | | |
|---|---|---|---|---|---|---|---|---|
| | | | | | | 37° C./4° C. | | |
| serum | 4° C. | 3 day | 7 day | 10 day | ref (605) | 3 day | 7 day | 10 day |
| H 156 | 1.952 | 1.831 | 1.814 | 1.825 | 1.530 | 0.938 | 0.929 | 0.935 |
| H 171 | 0.739 | 0.694 | 0.696 | 0.691 | 0.436 | 0.940 | 0.942 | 0.935 |
| H 130 | 0.742 | 0.675 | 0.663 | 0.675 | 0.821 | 0.910 | 0.893 | 0.910 |
| H 186 | 0.944 | 0.940 | 0.982 | 0.965 | 0.781 | 0.996 | 1.040 | 1.022 |
| H 203 | 0.995 | 0.968 | 1.049 | 1.055 | 0.806 | 0.972 | 1.054 | 1.060 |
| M92 + H 163 | 2.100 | 1.911 | 2.018 | 1.954 | 1.051 | 0.910 | 0.961 | 0.930 |
| F 111 | 0.281 | 0.258 | 0.251 | 0.255 | 0.214 | 0.918 | 0.891 | 0.906 |
| F 210 | 0.302 | 0.278 | 0.299 | 0.289 | 0.223 | 0.919 | 0.988 | 0.955 |

TABLE 11

| peptide Ct4C, blocker without sucrose with PBS. | | | | | | | | |
|---|---|---|---|---|---|---|---|---|
| | | | | | | 37° C./4° C. | | |
| serum | 4° C. | 3 day | 7 day | 10 day | ref (605) | 3 day | 7 day | 10 day |
| H 156 | 1.854 | 1.620 | 1.551 | 1.365 | 1.613 | 0.874 | 0.837 | 0.736 |
| H 171 | 0.708 | 0.617 | 0.591 | 0.504 | 0.444 | 0.872 | 0.835 | 0.712 |
| H 130 | 0.671 | 0.544 | 0.466 | 0.443 | 0.857 | 0.811 | 0.694 | 0.659 |
| H 186 | 0.946 | 0.863 | 0.754 | 0.749 | 0.790 | 0.912 | 0.797 | 0.791 |
| H 203 | 1.018 | 0.796 | 0.751 | 0.689 | 0.875 | 0.781 | 0.737 | 0.677 |
| M92 + H 163 | 2.099 | 1.776 | 1.581 | 1.390 | 1.342 | 0.846 | 0.753 | 0.662 |
| F 111 | 0.451 | 0.265 | 0.283 | 0.293 | 0.226 | 0.588 | 0.626 | 0.650 |
| F 210 | 0.271 | 0.309 | 0.339 | 0.296 | 0.226 | 1.140 | 1.249 | 1.092 |

TABLE 12

| peptide Ct4C, blocker without sucrose with PBS-T. | | | | | | | | |
|---|---|---|---|---|---|---|---|---|
| | | | | | | 37° C./4° C. | | |
| serum | 4° C. | 3 day | 7 day | 10 day | ref (605) | 3 day | 7 day | 10 day |
| H 156 | 1.879 | 1.370 | 1.310 | 1.221 | 1.571 | 0.729 | 0.697 | 0.650 |
| H 171 | 0.713 | 0.563 | 0.592 | 0.538 | 0.458 | 0.789 | 0.830 | 0.755 |
| H 130 | 0.633 | 0.407 | 0.389 | 0.421 | 0.805 | 0.643 | 0.615 | 0.666 |
| H 186 | 0.983 | 0.794 | 0.713 | 0.720 | 0.803 | 0.808 | 0.726 | 0.733 |
| H 203 | 1.062 | 0.751 | 0.749 | 0.703 | 0.871 | 0.707 | 0.705 | 0.662 |
| M92 + H 163 | 1.568 | 1.017 | 0.831 | 0.747 | 1.141 | 0.649 | 0.530 | 0.477 |
| F 111 | 0.276 | 0.306 | 0.261 | 0.252 | 0.244 | 1.107 | 0.946 | 0.913 |
| F 210 | 0.682 | 0.290 | 0.290 | 0.320 | 0.233 | 0.426 | 0.425 | 0.470 |

TABLE 13 peptide Ct4D, blocker with sucrose

| serum | 4° C. | 3 day | 7 day | 10 day | ref (605) | 37° C./4° C. 3 day | 7 day | 10 day |
|---|---|---|---|---|---|---|---|---|
| H 156 | 0.568 | 0.618 | 0.520 | 0.577 | 1.530 | 1.088 | 0.915 | 1.016 |
| H 171 | 0.542 | 0.543 | 0.536 | 0.544 | 0.429 | 1.003 | 0.989 | 1.004 |
| H 130 | 0.439 | 0.406 | 0.403 | 0.391 | 0.802 | 0.926 | 0.919 | 0.891 |
| H 186 | 0.712 | 0.726 | 0.726 | 0.713 | 0.769 | 1.019 | 1.020 | 1.001 |
| H 203 | 0.292 | 0.285 | 0.267 | 0.280 | 0.766 | 0.974 | 0.913 | 0.959 |
| M92 + H 163 | 0.372 | 0.351 | 0.368 | 0.345 | 1.248 | 0.943 | 0.991 | 0.927 |
| F 111 | 0.366 | 0.327 | 0.309 | 0.318 | 0.210 | 0.893 | 0.643 | 0.867 |
| F 210 | 0.352 | 0.333 | 0.322 | 0.335 | 0.221 | 0.945 | 0.915 | 0.950 |

TABLE 14 peptide Ct4D, blocker without sucrose with PBS.

| serum | 4° C. | 3 day | 7 day | 10 day | 37° C./4° C. 3 day | 7 day | 10 day |
|---|---|---|---|---|---|---|---|
| H 156 | 0.546 | 0.478 | 0.490 | 0.458 | 0.875 | 0.897 | 0.838 |
| H 171 | 0.570 | 0.504 | 0.506 | 0.458 | 0.883 | 0.887 | 0.804 |
| H 130 | 0.407 | 0.343 | 0.320 | 0.324 | 0.842 | 0.786 | 0.795 |
| H 186 | 0.736 | 0.639 | 0.572 | 0.680 | 0.868 | 0.777 | 0.923 |
| H 203 | 0.315 | 0.257 | 0.312 | 0.276 | 0.816 | 0.992 | 0.876 |
| M92 + H 163 | 0.361 | 0.326 | 0.360 | 0.345 | 0.903 | 0.999 | 0.956 |
| F 111 | 0.309 | 0.315 | 0.324 | 0.315 | 1.018 | 1.047 | 1.019 |
| F 210 | 0.307 | 0.307 | 0.319 | 0.333 | 1.000 | 1.039 | 1.083 |

TABLE 15 peptide Ct4d, blocker without sucrose with PBS-T.

| serum | 4° C. | 3 day | 7 day | 10 day | 37° C./4° C. 3 day | 7 day | 10 day |
|---|---|---|---|---|---|---|---|
| H 156 | 0.495 | 0.364 | 0.365 | 0.358 | 0.736 | 0.737 | 0.724 |
| H 171 | 0.510 | 0.425 | 0.447 | 0.410 | 0.834 | 0.877 | 0.805 |
| H 130 | 0.309 | 0.236 | 0.259 | 0.266 | 0.765 | 0.838 | 0.861 |
| H 186 | 0.751 | 0.647 | 0.573 | 0.508 | 0.861 | 0.763 | 0.676 |
| H 203 | 0.225 | 0.194 | 0.200 | 0.185 | 0.860 | 0.887 | 0.822 |
| M92 + H 163 | 0.337 | 0.323 | 0.336 | 0.603 | 0.957 | 0.996 | 1.789 |
| F 111 | 0.267 | 0.272 | 0.272 | 0.280 | 1.019 | 1.019 | 1.051 |
| F 210 | 0.282 | 0.292 | 0.290 | 0.293 | 1.037 | 1.028 | 1.041 |

In order to find out whether the presence of sucrose in the blocking buffer only affects *C. trachomatis* peptides (all of the tested peptides were from the VDIV region of the MOMP protein and therefore homologous in their sequence), or also affects the stability of other peptides, various peptides derived from the MOMP protein sequence of *C. pneumoniae* were tested for stability as described above for *C. trachomatis* peptides.

When sucrose was present in the blocking buffer, peptides *C.p*VDM, *C.p*1A were essentially stable (see Tables 16, 22). Also a mixture of peptides (*C.p*1A, *C.p*2A, *C.p*VDIII. *C.p*4A), was stable (Table 19). Peptide *C.p*2A was somewhat less stable under these conditions, as indicated by ratios (37÷C/4÷C) ranging between 0.8 and 0.9 with four of the sera tested (Table 25, M92, H171+H226, H171, H247 after ten days storage).

When sucrose was omitted from the blocking solution, however, the stability of the reactivity of the peptides was reduced for two sera in the case of *C.p* VDIII (Table 17), for five sera in the case of the peptide mixture (Table 20), and for four sera in the case of *C.p* 1A (Table 23). The slight instability of peptide *C.p*2A observed with sucrose-containing buffer (Table 25, ratios between 0.8 and 0.9 for M92, H171+H226, H171 and H156) was significantly increased when sucrose was omitted from the buffer (Table 26, ratios between 0.5 and 0.8 for the same sera).

The addition of TWEEN-20 to the blocking solution as customary in the art of ELISA further reduced the stability of the *C. pneumoniae* peptides, as can be seen for *C.p* VDIII (compare Table 18 to Table 17), and the peptide mixture (compare Table 21 to Table 20). On the other hand, the stability of *C.p*1A was unaffected by the presence of TWEEN in the blocking buffer (compare Table 24 to Table 23), while TWEEN even seemed to have a beneficial effect on the stability of *C.p*2A (compare Table 27 to Table 26, sera M92 and H1163). However, even in the case of *C.p*2A, the addition of sucrose was superior to the addition of TWEEN with regard to enhanced stability (compare e.g. sera M95 and H163 in Tables 25–27).

In summary, the above experiments suggest that the *C. trachomatis* and *C. pneumoniae* peptides used herein display several epitopes, that these epitopes are independently affected by storage without sucrose and by the addition of TWEEN into the blocking solution. They further suggest that storage without sucrose may lead to the exposure or formation of epitopes that bind unspecifically, giving rise to high background levels and therefore raising the likelihood to obtain a false-positive output in the assay. In very rare cases, the addition of TWEEN-20 may help to stabilize a specific epitope, as in the case of reactivity of *C.p*2A to H163 (compare Tables 30 and 29). The omission of TWEEN-20 and the addition of sucrose to the blocking buffer, which is in contrast to the current understanding in the art of ELISA, overcome all these problems. This is demonstrated using a variety of peptides that are derived from different areas (VD1, VDII and VDIV) of the MOMP of two different Chlamydia strains. The peptides therefore have no common structure or sequence homology, so that the results obtained here are likely to be valid for peptides in general.

TABLE 16

C.p2, blocker with sucrose

| serum | 4° C. | 3 day | 1 week | 10 day | 37° C./4° C. 3 day | 1 week | 10 day |
|---|---|---|---|---|---|---|---|
| M 92 | 0.488 | 0.462 | 0.448 | 0.482 | 0.946 | 0.917 | 0.988 |
| H 171 + | 0.497 | 0.534 | 0.476 | 0.479 | 1.074 | 0.958 | 0.963 |

TABLE 16-continued

C.p2, blocker with sucrose

| | | | | | 37° C./4° C. | | |
|---|---|---|---|---|---|---|---|
| serum | 4° C. | 3 day | 1 week | 10 day | 3 day | 1 week | 10 day |
| H 228 | | | | | | | |
| H 228 | 0.448 | 0.476 | 0.414 | 0.415 | 1.061 | 0.923 | 0.926 |
| H 163 | 0.720 | 0.672 | 0.692 | 0.692 | 0.933 | 0.962 | 0.961 |
| H 171 | 0.488 | 0.511 | 0.490 | 0.494 | 1.047 | 1.003 | 1.011 |
| H 247 | 0.590 | 0.553 | 0.537 | 0.542 | 0.938 | 0.910 | 0.919 |
| H 156 | 0.371 | 0.356 | 0.366 | 0.368 | 0.960 | 0.985 | 0.991 |
| H 203 | 0.185 | 0.186 | 0.188 | 0.223 | 1.005 | 1.019 | 1.206 |

TABLE 17

C.p2, blocker without sucrose with PBS.

| | | | | | 37° C./4° C. | | |
|---|---|---|---|---|---|---|---|
| serum | 4° C. | 3 day | 1 week | 10 day | 3 day | 1 week | 10 day |
| M 92 | 0.499 | 0.409 | 0.434 | 0.409 | 0.819 | 0.870 | 0.820 |
| H 171 + H 228 | 0.477 | 0.641 | 0.425 | 0.436 | 1.343 | 0.891 | 0.914 |
| H 228 | 0.461 | 0.421 | 0.455 | 0.537 | 0.913 | 1.052 | 1.166 |
| H 163 | 0.753 | 0.768 | 0.581 | 0.590 | 1.019 | 0.771 | 0.783 |
| H 171 | 0.480 | 0.437 | 0.448 | 0.455 | 0.910 | 0.934 | 0.948 |
| H 247 | 0.597 | 0.555 | 0.553 | 0.605 | 0.929 | 0.926 | 1.013 |
| H 156 | 0.357 | 0.352 | 0.335 | 0.366 | 0.986 | 0.935 | 1.025 |
| H 203 | 0.191 | 0.199 | 0.213 | 0.288 | 1.039 | 1.115 | 1.505 |

TABLE 18

C.p2, blocker without sucrose with PBS-T.

| | | | | | 37° C./4° C. | | |
|---|---|---|---|---|---|---|---|
| serum | 4° C. | 3 day | 1 week | 10 day | 3 day | 1 week | 10 day |
| M 92 | 0.545 | 0.413 | 0.416 | 0.406 | 0.758 | 0.763 | 0.744 |
| H 171 + H 228 | 0.495 | 0.415 | 0.405 | 0.422 | 0.837 | 0.817 | 0.852 |
| H 228 | 0.462 | 0.427 | 0.454 | 0.493 | 0.925 | 0.983 | 1.067 |
| H 163 | 0.749 | 0.607 | 0.579 | 0.591 | 0.810 | 0.774 | 0.790 |
| H 171 | 0.636 | 0.416 | 0.420 | 0.414 | 0.654 | 0.661 | 0.651 |
| H 247 | 0.585 | 0.558 | 0.514 | 0.538 | 0.954 | 0.879 | 0.920 |
| H 156 | 0.328 | 0.313 | 0.322 | 0.326 | 0.953 | 0.980 | 0.994 |
| H 203 | 0.200 | 0.215 | 0.200 | 0.228 | 1.075 | 1.000 | 1.138 |

TABLE 19

CP MIX, blocker with sucrose

| | | | | | 37° C./4° C. | | |
|---|---|---|---|---|---|---|---|
| serum | 4° C. | 3 day | 1 week | 10 day | 3 day | 1 week | 10 day |
| M 92 | 2.528 | 2.452 | 2.486 | 2.498 | 0.970 | 0.983 | 0.988 |
| H 171 + H 228 | 0.445 | 0.521 | 0.568 | 0.517 | 1.172 | 1.277 | 1.163 |
| H 228 | 2.126 | 2.136 | 2.075 | 2.190 | 1.005 | 0.976 | 1.030 |
| H 163 | 1.180 | 1.172 | 1.192 | 1.210 | 0.994 | 1.010 | 1.026 |
| H 171 | 0.712 | 0.746 | 0.721 | 0.745 | 1.048 | 1.013 | 1.046 |
| H 247 | 0.721 | 0.710 | 0.734 | 0.735 | 0.984 | 1.017 | 1.019 |
| H 156 | 0.249 | 0.272 | 0.271 | 0.235 | 1.093 | 1.089 | 0.944 |
| H 203 | 0.137 | 0.157 | 0.138 | 0.143 | 1.147 | 1.007 | 1.044 |

TABLE 20

CP MIX, blocker without sucrose with PBS.

| | | | | | 37° C./4° C. | | |
|---|---|---|---|---|---|---|---|
| serum | 4° C. | 3 day | 1 week | 10 day | 3 day | 1 week | 10 day |
| M 92 | 2.65 | 2.33 | 1.72 | 1.96 | 0.88 | 0.65 | 0.74 |
| H 171 + H 228 | 0.55 | 0.41 | 0.38 | 0.52 | 0.75 | 0.69 | 0.94 |
| H 228 | 2.09 | 1.84 | 1.76 | 1.70 | 0.88 | 0.84 | 0.82 |
| H 163 | 1.17 | 0.93 | 0.87 | 0.88 | 0.79 | 0.74 | 0.75 |
| H 171 | 0.63 | 0.49 | 0.43 | 0.45 | 0.78 | 0.68 | 0.71 |
| H 247 | 0.71 | 0.57 | 0.51 | 0.52 | 0.81 | 0.72 | 0.73 |
| H 156 | 0.23 | 0.22 | 0.24 | 0.25 | 0.96 | 1.01 | 1.05 |
| H 203 | 0.16 | 0.16 | 0.17 | 0.19 | 1.00 | 1.02 | 1.19 |

TABLE 21

CP MIX, blocker without sucrose with PBS-T.

| | | | | | 37° C./4° C. | | |
|---|---|---|---|---|---|---|---|
| serum | 4° C. | 3 day | 1 week | 10 day | 3 day | 1 week | 10 day |
| M 92 | 2.601 | 1.734 | 1.448 | 1.262 | 0.667 | 0.557 | 0.485 |
| H 171 + H 228 | 0.668 | 0.431 | 0.386 | 0.424 | 0.644 | 0.577 | 0.635 |
| H 228 | 2.071 | 1.754 | 1.475 | 1.446 | 0.847 | 0.712 | 0.698 |
| H 163 | 1.094 | 0.831 | 0.734 | 0.703 | 0.760 | 0.671 | 0.643 |
| H 171 | 0.711 | 0.558 | 0.439 | 0.578 | 0.785 | 0.617 | 0.813 |
| H 247 | 0.684 | 0.459 | 0.466 | 0.417 | 0.671 | 0.682 | 0.610 |
| H 156 | 0.257 | 0.276 | 0.267 | 0.243 | 1.074 | 1.041 | 0.945 |
| H 203 | 0.148 | 0.166 | 0.165 | 0.172 | 1.122 | 1.119 | 1.163 |

TABLE 22

C.p1A, blocker with sucrose

| | | | | | 37° C./4° C. | | |
|---|---|---|---|---|---|---|---|
| serum | 4° C. | 3 day | 1 week | 10 day | 3 day | 1 week | 10 day |
| M 92 | 1.830 | 1.749 | 1.732 | 1.729 | 0.955 | 0.946 | 0.945 |
| H 171 + H 226 | 0.875 | 0.885 | 0.803 | 0.837 | 1.011 | 0.918 | 0.957 |
| H 228 | 2.272 | 2.278 | 2.233 | 2.243 | 1.003 | 0.983 | 0.987 |
| H 163 | 1.300 | 1.315 | 1.295 | 1.320 | 1.012 | 0.996 | 1.015 |
| H 171 | 0.471 | 0.484 | 0.575 | 0.472 | 1.029 | 1.222 | 1.003 |
| H 247 | 0.658 | 0.669 | 0.681 | 0.635 | 1.017 | 1.035 | 0.965 |
| H 156 | 0.591 | 0.552 | 0.573 | 0.548 | 0.935 | 0.970 | 0.928 |
| H 203 | 0.242 | 0.299 | 0.269 | 0.276 | 1.236 | 1.112 | 1.140 |

TABLE 23

C.p1A, blocker without sucrose with PBS.

| | | | | | 37° C./4° C. | | |
|---|---|---|---|---|---|---|---|
| serum | 4° C. | 3 day | 1 week | 10 day | 3 day | 1 week | 10 day |
| M 92 | 1.593 | 1.143 | 0.865 | 0.798 | 0.717 | 0.543 | 0.501 |
| H 171 + H 226 | 0.719 | 0.603 | 0.529 | 0.554 | 0.839 | 0.736 | 0.770 |
| H 228 | 2.119 | 1.771 | 1.407 | 1.421 | 0.836 | 0.664 | 0.671 |
| H 163 | 1.146 | 0.980 | 0.831 | 0.753 | 0.855 | 0.725 | 0.657 |
| H 171 | 0.429 | 0.475 | 0.474 | 0.399 | 1.106 | 1.105 | 0.929 |
| H 247 | 0.623 | 0.544 | 0.566 | 0.547 | 0.872 | 0.908 | 0.877 |
| H 156 | 0.465 | 0.450 | 0.460 | 0.445 | 0.968 | 0.990 | 0.957 |
| H 203 | 0.253 | 0.245 | 0.214 | 0.234 | 0.966 | 0.844 | 0.923 |

TABLE 24

C.p1A, blocker without sucrose with PBS-T.

| serum | 4° C. | 3 day | 1 week | 10 day | 37° C./4° C. 3 day | 1 week | 10 day |
|---|---|---|---|---|---|---|---|
| M 92 | 1.574 | 0.878 | 0.813 | 0.737 | 0.558 | 0.517 | 0.468 |
| H 171 + H 226 | 0.803 | 0.628 | 0.776 | 0.693 | 0.783 | 0.967 | 0.863 |
| H 228 | 2.129 | 1.681 | 1.554 | 1.466 | 0.790 | 0.730 | 0.689 |
| H 163 | 1.145 | 0.892 | 0.811 | 0.748 | 0.779 | 0.708 | 0.653 |
| H 171 | 0.395 | 0.476 | 0.423 | 0.467 | 1.204 | 1.070 | 1.181 |
| H 247 | 0.594 | 0.520 | 0.478 | 0.579 | 0.875 | 0.805 | 0.975 |
| H 156 | 0.524 | 0.430 | 0.467 | 0.471 | 0.820 | 0.890 | 0.898 |
| H 203 | 0.231 | 0.336 | 0.291 | 0.268 | 1.458 | 1.262 | 1.163 |

TABLE 25

C.pA2, blocker with sucrose

| serum | 4° C. | 3 day | 1 week | 10 day | 37° C./4° C. 3 day | 1 week | 10 day |
|---|---|---|---|---|---|---|---|
| M 92 | 2.703 | 2.539 | 2.307 | 2.151 | 0.939 | 0.853 | 0.7956 |
| H 171 + H 226 | 0.815 | 0.786 | 0.842 | 0.714 | 0.964 | 1.033 | 0.8761 |
| H 228 | 0.686 | 0.644 | 0.627 | 0.638 | 0.939 | 0.914 | 0.9300 |
| H 163 | 0.550 | 0.672 | 0.582 | 0.677 | 1.221 | 1.058 | 1.2309 |
| H 171 | 1.062 | 1.108 | 0.899 | 0.888 | 1.043 | 0.847 | 0.8357 |
| H 247 | 0.608 | 0.535 | 0.507 | 0.522 | 0.880 | 0.833 | 0.8586 |
| H 156 | 0.487 | 0.480 | 0.448 | 0.497 | 0.986 | 0.920 | 1.0205 |
| H 203 | 0.247 | 0.415 | 0.264 | 0.241 | 1.678 | 1.067 | 0.9757 |

TABLE 26

C.p2A, blocker without sucrose with PBS.

| serum | 4° C. | 3 day | 1 week | 10 day | 37° C./4° C. 3 day | 1 week | 10 day |
|---|---|---|---|---|---|---|---|
| M 92 | 2.518 | 1.927 | 1.548 | 1.477 | 0.765 | 0.615 | 0.587 |
| H 171 + H 226 | 0.714 | 0.576 | 0.598 | 0.528 | 0.807 | 0.837 | 0.740 |
| H 228 | 0.585 | 0.504 | 0.487 | 0.561 | 0.862 | 0.833 | 0.959 |
| H 163 | 0.503 | 0.461 | 0.409 | 0.371 | 0.916 | 0.813 | 0.738 |
| H 171 | 0.875 | 0.785 | 0.722 | 0.636 | 0.897 | 0.825 | 0.727 |
| H 247 | 0.498 | 0.487 | 0.490 | 0.490 | 0.978 | 0.984 | 0.985 |
| H 156 | 0.360 | 0.378 | 0.371 | 0.367 | 1.050 | 1.031 | 1.021 |
| H 203 | 0.176 | 0.182 | 0.186 | 0.192 | 1.034 | 1.054 | 1.091 |

TABLE 27

C.p2A, blocker without sucrose with PBS-T.

| serum | 4° C. | 3 day | 1 week | 10 day | 37° C./4° C. 3 day | 1 week | 10 day |
|---|---|---|---|---|---|---|---|
| M 92 | 2.606 | 1.852 | 1.703 | 1.692 | 0.711 | 0.654 | 0.649 |
| H 171 + H 226 | 0.729 | 0.551 | 0.521 | 0.520 | 0.756 | 0.714 | 0.714 |
| H 228 | 0.634 | 0.525 | 0.764 | 0.514 | 0.828 | 1.205 | 0.810 |
| H 163 | 0.470 | 0.502 | 0.355 | 0.503 | 1.067 | 0.754 | 1.070 |
| H 171 | 0.943 | 0.792 | 0.659 | 0.646 | 0.840 | 0.699 | 0.685 |
| H 247 | 0.503 | 0.414 | 0.402 | 0.437 | 0.824 | 0.800 | 0.870 |
| H 156 | 0.350 | 0.318 | 0.290 | 0.316 | 0.910 | 0.830 | 0.903 |
| H 203 | 0.173 | 0.354 | 0.185 | 0.172 | 2.049 | 1.070 | 0.994 |

Development and Characterization of a Diagnostic Kit Specific for *C. trachomatis*

The diagnostic kits developed in accordance with the present invention are essentially improved Enzyme-Linked Immunosorbent Assay (ELISA) kits designed specifically for the diagnosis of *C. trachomatis*-specific infections. Two basic kits have been developed, both being manipulatable to vary several of the constituents thereof to meet the users' needs. One kit is intended for the determination of specific *C. trachomatis* IgG antibodies in human sera, this being designated herein as the "IgG kit". The second kit is intended for the determination of specific *C. trachomatis* IgA antibodies in human sera, this being designated herein as the "IgA kit". Generally, the above kits of the invention will have at least some of the following constituents:

(i) A *C. trachomatis* antigen-coated microtiter plate with a plate cover, usually of the standard multiwell type having 96 wells per plate arranged in the form of 12 columns and 8 rows, i.e., 8 wells per column for a total of 96 wells. With such plates, there will be provided 12 removable 8-well strips coated with the *C. trachomatis* antigen. The *C. trachomatis* antigen will preferably be a mixture of new peptides as set forth in Example 1 above, the most preferred mixtures being those designated in Example 1 as "MIX 1" and "MIX 2". Hence, for each well of the microtiter plate, there will be a strip coated with the *C. trachomatis* peptide mixture of the invention.

(ii) A concentrated wash buffer, usually being a concentrated PBS-TWEEN buffer of the standard type well known in the art.

(iii) A serum diluent, usually in the form of a ready-to-use colored buffer solution.

(iv) A conjugate diluent, usually in the form of a ready-to-use colored buffer solution.

(v) A negative control which is usually a *C. trachomatis* IgG or IgA negative human serum in a ready-to-use form.

(vi) A positive control which is usually a *C. trachomatis* IgG or IgA positive human serum in a ready-to-use form.

(vii) A concentrated HRP-conjugate, usually in the form of horseradish peroxidase (HRP) conjugated to anti-human IgG or anti-human IgA (gamma chain specific).

(viii) A concentrated TMB-substrate, usually in the form of 3,3',5,5'-tetramethyl-benzidine (TMB) in dimethylsulfoxide (DMSO) as chromagen and urea hydrogen peroxide as substrate for peroxidase (HRP).

(ix) A stop solution, usually containing 1 M $H_2SO_4$ in a ready-to-use form.

(x) Detailed instructions for use, inclusive of warnings and precautions. Of all of the above constituents, those unique to the present invention, and hence essential to the kits of the invention, are: (i) the *C. trachomatis* peptide mixture-coated microtiter plate, and (x) the detailed instructions for use. All the other constituents, (ii)–(ix) may be the improved or modified ones noted below in accordance with the invention, or standard, commercially available equivalents well known in the art of ELISA.

Using the above kits and new mixtures of *C. trachomatis* peptides, the basic assay procedure is as follows:

(a) Assay Procedure

1. Incubation of the sera samples and controls:

1.1 Dilute each patient serum 1/21 with the serum diluent (commercially available and usually supplied with the kit; see also below).

1.2 Pipette 50 μl from positive control, negative control and from the patient serum diluted 1/21 (from step 1.1) into separate wells of the test strip (as noted above, each strip is an antigen-coated 8-well strip, with a possibility of 12 such strips per microtiter plate when using 96-well plates).

1.3 Cover the strips (i.e., cover the whole plate with the plate cover) and incubate for 1 hour at 37° C. in a humidified environment.

1.4 Discard the liquid contents of the wells.

1.5 Washing step: Fill each well with wash buffer and discard the liquid; repeat this step six times.

1.6 Dry the strips and ELISA plate, gently tapping them over clean absorbent paper.

2. Incubation with conjugate:

2.1 Dilute the concentrated (usually 300× concentrated) HRP conjugate anti-human IgG 1/300 with conjugate diluent.

2.2 Pipette 50 μl of diluted conjugate into each well.

2.3 Cover the strips and incubate for one hour at 37° C. in a humidified environment.

2.4 Discard the liquid content and wash as described in step 1.5.

2.5 Dry the strips and ELISA plate by gently tapping them over clean absorbent paper.

3. Incubation with TMB substrate:

3.1 Dilute the concentrated (usually 10× concentrated) TMB-Substrate 1/10 in DDW. Alternatively, ready-to-use (RTU)-TMB substrate may be used, and the dilution step omitted.

3.2 Pipette 100 μl of diluted TMB-Substrate into each well, cover the strips and incubate at room temperature for 10 minutes only. Alternatively, the RTU-TMB substrate may be used, and incubation extended to 15 minutes.

3.3 Stop the reaction by adding 100 μl of IM $H_2SO_4$ (chromogen stop solution) to each well.

3.4 Determine the absorbance at 450 nm and record the results.

b) Development of Improved Serological Diagnostic Kits:

The following is an outline of the development of the improved kits:

1) Making the Kits More "user friendly":

a. Reducing the number of washing steps.

b. Adding different colors to the serum diluent and the conjugate diluent.

c. Stabilizing the kit for longer shelf life.

2) Clinical evaluations of the improved kits.

In order to achieve goal 1a) above, namely, to reduce the number of washing steps from six to three, different wash buffers were tested and compared to the original one usually used in ELISA, which is a PBS-based buffer. These wash buffers contained an increasing amount of non-ionic detergents, or ionic detergents.

Results: The wash buffer that enabled only three washing steps was the one that contained non-ionic detergent, this being the above-noted PBS-TWEEN buffer (see constituent no. (ii) in the above list). Further, it was found that this PBS-TWEEN buffer could be readily prepared in a preferred concentration of 20× concentrated, which 20× concentrated wash buffer was stable for one month at 37° C. and for 11 months at 4° C.

To achieve the goal set forth in 1b) above, the following was carried out:

The following colors were added either to the serum diluent or to the conjugate diluent and tested: violet powder, evans blue, mocca brown powders and from the food colors: blue brilliant, yellow sunset and their combination (green color).

Results: The violet, evans blue and mocca brown colors had some interference with the test, by either increasing the background signal and/or decreasing the actual test signal. The only colors that worked well in the test were the blue brilliant, yellow sunset and their combination (green color).

It should also be noted that the blue brilliant and yellow sunset colors and their combination (green color) were stable for one month at 37° C. and for one year at 4° C. Based on these results, in the preferred kits of the invention, the serum diluent is provided with blue color and the conjugate diluent is provided with green color, thereby providing for optimal distinction between the two diluents on a color basis, while at the same time, these colors do not interfere with the assay.

Regarding the goal of 1c above, it was found that RTU-TMB substrate was stable for one month at 37÷C and for 12 months at 4÷C. This is also the case for the other reagents used in the improved kit, as mentioned above.

In order to attain goal 5 above, namely, clinical evaluations of the IgG and IgA *C. trachomatis* kits, the following was performed:

1) Comparison of the sensitivity and specificity of IgG and IgA kits as compared to MIF MRL:

To evaluate the sensitivity and the specificity of the IgG and IgA kits, sera from uninfected individuals (negative sera), or those already determined to have been positively infected with only *C. trachomatis* (positive sera) were tested according to the above procedure concerning carrying out the assay procedure using the kits. The sensitivity and specificity were calculated as compared to the results obtained by MWF MRL (a commercially available, standard microimmunofluorescence (MIF) assay kit used in accordance with the manufacturer's instructions and employing the relevant *C. trachomatis* antigens for detecting the IgG and IgA antibodies in the sera).

Figure 10:
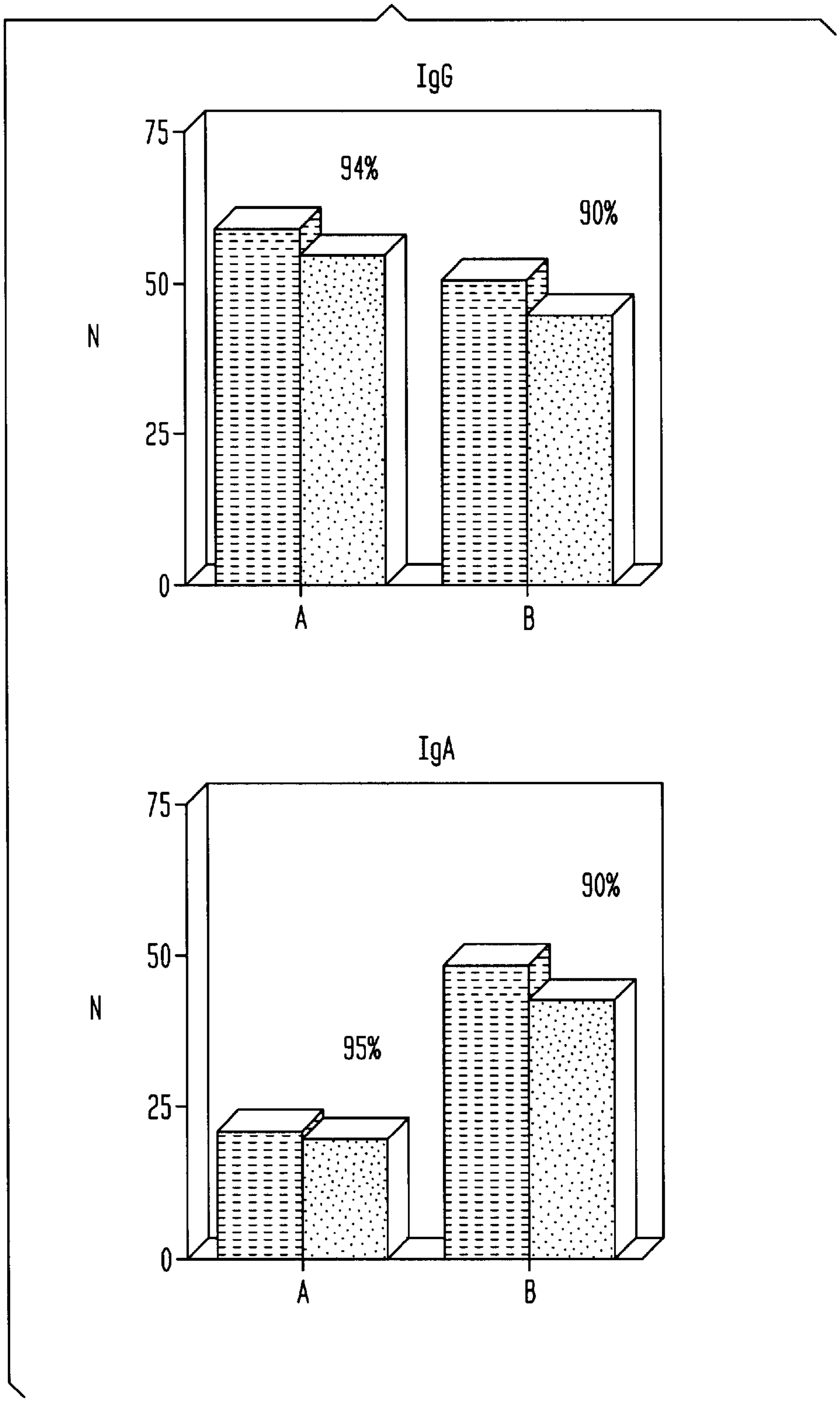
FIG. 10 are bar graph representations illustrating the sensitivity and specificity of the mixture of new peptides specific for *C. trachomatis* used in ELISA assays to detect anti-MOMP IgG and IgA antibodies specific to *C. trachomatis* MOMP and the comparison of this assay with a MIF assay, as described in Example 2. N, number of tested sera; A, positive sera, B, negative sera, bars filled with interrupted stripes, sera characterized positive by MIF (commercial reference), filled bars, sera characterized by *C.trachomatis* peptide assay.

Results: The IgG and IgA kits are able to detect both IgG and IgA levels in sera from *C. trachomatis*-infected individuals as determined by MWF MRL. The sensitivity and specificity of the peptide assay are high and were 94% and 90%, respectively, for IgG and 95% and 90%, for IgA. These results are summarized in FIG. 10, in which the light bars in the bar graphs represent the results obtained with the MIF-commercial reference kit and the dark bars represent the results obtained with the IgG kit (left hand graph) and with the IgA kit (right hand graph).

Comparison of the sensitivity and specificity of IgG and IgA kits as compared to Culture Human sera from individuals infected with *C. trachomatis* as determined by culture were tested for *C. trachomatis* IgG and IgA antibodies with the IgG and IgA kits. Sera which were IgG negative were also tested by another serological test, MIF (as noted above). The sensitivity of the IgG and IgA kits were compared to culture.

Figure 11:
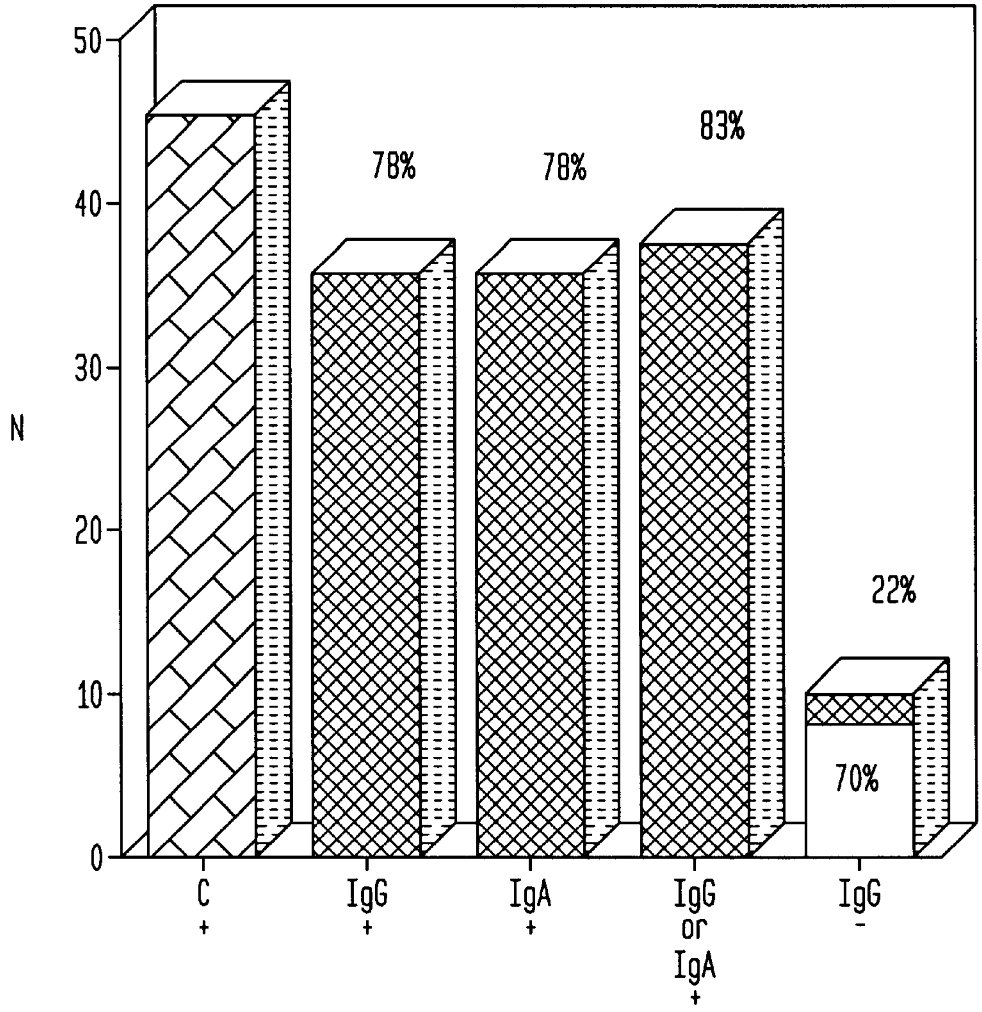
FIG. 11 is a bar graph representation illustrating the sensitivity and specificity of the mixture of new peptides specific for *C. trachomatis* used in an ELISA assay to detect anti-MOMP IgA and/or IgG antibodies specific to *C. trachomatis* MOMP and the comparison of this assay with a culture assay as described in Example 2. N, number of individuals tested; C, culture, brick-pattern filled bars, sera characterized positive by culture assay, cross-striped bars, sera characterized by *C. trachomatis* peptide essay, empty bar, sera characterized by MIF.

Results: The results are summarized in FIG. 11, from which it is apparent that the sensitivity of *C. trachomatis* assay (dark bars in FIG. 11), as compared to culture (hatched bar in FIG. 11) was 78% for IgG and 78% for IgA. Five percent of the sera showed only IgA reactivity. Therefore, the overall sensitivity of the kits was calculated to be 83%. 70% of the sera that were negative for IgG (22% of the total sera) were also negative by MIF (open bar, FIG. 11).

c) The Specificity of the IgG Kit as Compared to Different MWF Tests

The specificity of the IgG kit was determined, as compared to different MIF tests (MIF1, MWF2 and SeroFIA tests). All the MIF-tested sera were *C. trachomatis* negative (*C.t*–) and a portion of the sera were also *C. pneumoniae* positive sera (*C.t*/*C.p*+). MIF1 and MIF2 are standard MIF tests as noted above, while SeroFIA is a new microimmunofluorescence test for the differential detection of *C. trachomatis, C. pneumoniae* and *C. psittaci.*

Figure 12:
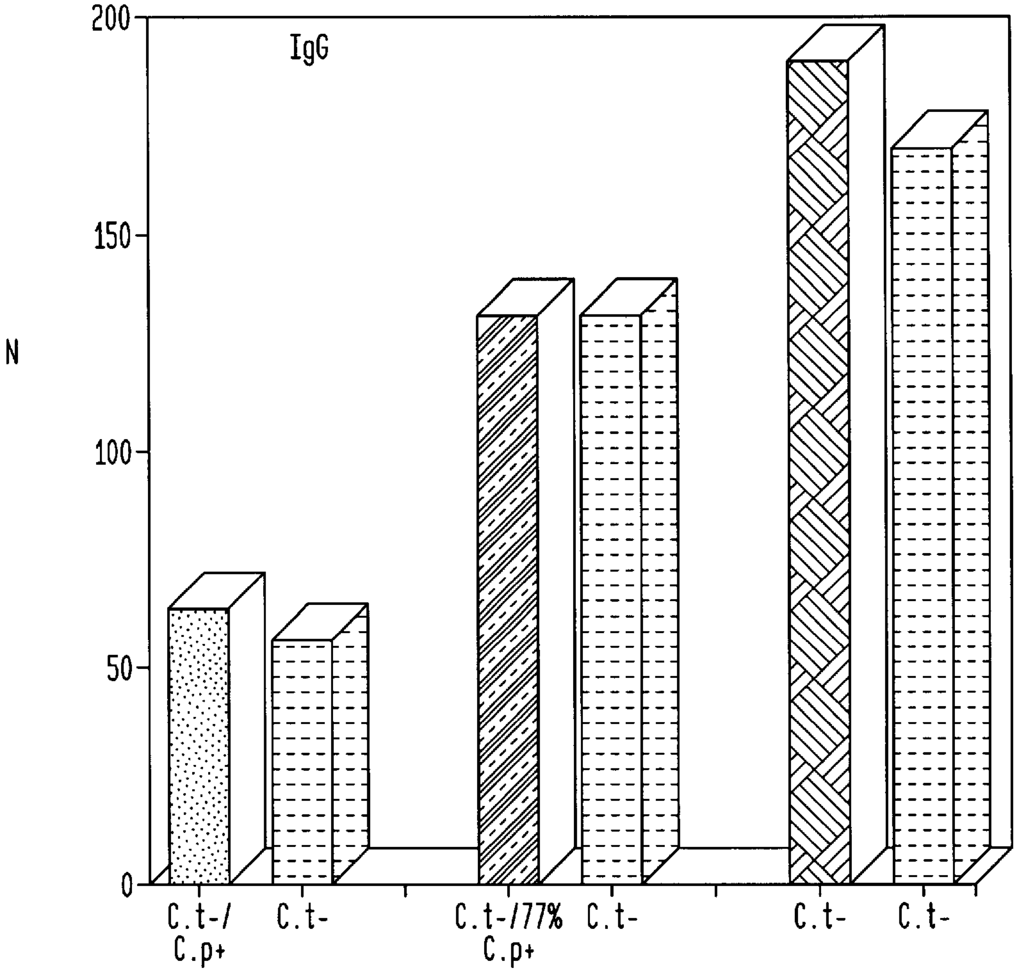
FIG. 12 is a bar graph representation illustrating the specificity and of a mixture of new peptides (*C.t*4A, 4C, 4B, 4D)specific for *C. trachomatis* used in an ELISA assay to detect anti-MOMP IgA and/or IgG antibodies specific to *C. trachomatis* MOMP and a comparison of this assay with a number of different MIF assays, as described in Example 2. N, number of tested sera; Filled bar, sera tested positive by MIF 1 assay, bars filled by interrupted stripes, sera tested positive by *C. trachomatis* peptide assay, bar filled with double and interrupted lines, sera tested positive by SeroFIA assay (Savyon), cross-hatched bar, sera tested positive by MIF 2 assay.

Results: The results are summarized in FIG. 12, from which it is apparent that the IgG kit is highly specific, and showed at least 90% specificity (light bars in FIG. 12), as compared to the various MIF assays (dark bars and dark/hatched bars in FIG. 12). The IgG kit did not cross-react with *C. pneumoniae* positive sera.

Based on all of the above-mentioned concerning the sensitivity and specificity of the IgG and IgA kits of the invention, it is advantageous when using these kits to assay serum samples, to use both kits, namely, to subject each serum sample to the IgG and the IgA tests, and then to compare the results. In this way, there is provided a further check with respect to the accuracy of the test results, thus further ensuring that false-negative and/or false-positive results are not obtained. The following Table 28 provides an outline for evaluating the results and interpreting them when testing sera with both the IgG and IgA kits:

TABLE 28

Significance of results based on the combination of IgA and IgG antibodies, as obtained using both IgG and IgA kits to test each serum sample

| Levels of Chlamydia antibodies | | |
|---|---|---|
| | IgG | Significance of Results |
| Negative | Negative | Negative (or beyond the sensitivity ofthis test) |
| Negative | Positive | Indication of specific IgB antibodies. May mean past or current infection. |
| Borderline | Low positive or borderline | Second sample testing is required after 14–21 days. |
| Positive | Positive, low positive or borderline | Presence of specific IgA and IgG antibodies. Indicates current or recent or chronic infection. |
| Positive | Negative | Presence of IgA antibodies may indicate current or chronic infection. |

What is claimed is:

1. A mixture of peptides comprising at least two peptide sequences selected from the group of peptides consisting of (a) IFDTTLNPTIAGAGDVK (SEQ ID NO:1);

(b) VDITTLNPTIAGCGSVAK (SEQ ID NO:2);

(c) CVFDVTTLNPTIAGAGDVK (SEQ. ID NO:3); and (d) LAEAILDVT-LNPTI-GKAVVSK (SEQ. ID NO:4).

2. The mixture of peptides of claim 1, comprising all 4 of said peptides.

3. The mixture of peptides of claim 1 comprising said peptides (a), (b), (c) and (d), each in equal amounts.

4. A composition comprising the mixture of peptides of claim 1 conjugated with a detectable marker.

5. A composition comprising the mixture of the peptides of claim 1 and a carrier.

6. A kit for the diagnosis of *C. trachomatis* infection comprising the mixture of peptides of claim 1 and manufacturer's instructions for use of said kit.

7. The kit of claim 6 further comprising reagents for conducting an RIA, EIA, ELISA, Immuno competition assay or lateral chromatography assay.

8. The kit of claim 6 wherein said mixture of peptides is immobilized on a solid support and further comprises reagents for conducing an ELISA.

* * * * *

UNITED STATES PATENT AND TRADEMARK OFFICE

CERTIFICATE OF CORRECTION

PATENT NO. : 6,699,678 B1
DATED : March 2, 2004
INVENTOR(S) : Bella Ohana

It is certified that error appears in the above-identified patent and that said Letters Patent is hereby corrected as shown below:

Column 1,
Line 32, "*pneumonziae*", should read -- *pneumoniae* --.

Column 7,
Line 8, "N", should read -- N- --.

Column 21,
Line 48, insert -- B) Results obtained using C. *pneumoniae* peptides --.
Line 57, "VDM", should read -- VDIII --.

Column 29,
Line 2, "MWF", should read -- MIF --.

Column 30,
Line 10, insert -- IgA -- over first column.
Line 13, "ofthis", should read -- of this --.
Line 14, "IgB" should read -- IgG --.

Column 33,
Line 61, "(d) LAEAILDVT-LNPTI-GKAVVSK (SEQ. ID NO:4)" should read -- (d) LAEAILDVTTLNPTITGKAVVSK (SEQ. ID NO:4) --.

Signed and Sealed this

Twentieth Day of July, 2004

JON W. DUDAS
*Acting Director of the United States Patent and Trademark Office*